United States Patent
Hattori et al.

(10) Patent No.: US 10,975,104 B2
(45) Date of Patent: Apr. 13, 2021

(54) BORON-CONTAINING COMPOUND

(71) Applicants: Stella Pharma Corporation, Osaka (JP); Osaka Prefecture University Public Corporation, Osaka (JP)

(72) Inventors: Yoshihide Hattori, Osaka (JP); Kohki Uehara, Osaka (JP); Mitsunori Kirihata, Osaka (JP)

(73) Assignees: STELLA PHARMA CORPORATION, Osaka (JP); OSAKA PREFECTURE UNIVERSITY PUBLIC CORPORATION, Osaka (JP)

( * ) Notice: Subject to any disclaimer, the term of this patent is extended or adjusted under 35 U.S.C. 154(b) by 0 days.

(21) Appl. No.: 16/320,989

(22) PCT Filed: Jul. 20, 2017

(86) PCT No.: PCT/JP2017/026272
§ 371 (c)(1),
(2) Date: Jan. 25, 2019

(87) PCT Pub. No.: WO2018/021138
PCT Pub. Date: Feb. 1, 2018

(65) Prior Publication Data
US 2019/0177341 A1 Jun. 13, 2019

(30) Foreign Application Priority Data
Jul. 28, 2016 (JP) .............................. JP2016-148978

(51) Int. Cl.
| | | |
|---|---|---|
| C07F 5/05 | (2006.01) | |
| A61K 41/00 | (2020.01) | |
| A61K 31/69 | (2006.01) | |
| A61K 47/24 | (2006.01) | |
| C07H 23/00 | (2006.01) | |
| A61P 35/00 | (2006.01) | |

(52) U.S. Cl.
CPC ............... *C07F 5/05* (2013.01); *A61K 31/69* (2013.01); *A61K 41/00* (2013.01); *A61K 41/0095* (2013.01); *A61K 47/24* (2013.01); *A61P 35/00* (2018.01); *C07H 23/00* (2013.01)

(58) Field of Classification Search
None
See application file for complete search history.

(56) References Cited

U.S. PATENT DOCUMENTS

| | | |
|---|---|---|
| 8,907,128 B2 | 12/2014 | Kirihata et al. |
| 2002/0160969 A1 | 10/2002 | Schinazi et al. |
| 2009/0227539 A1 | 9/2009 | Olsson et al. |
| 2009/0317920 A1 | 12/2009 | Kirihata et al. |
| 2011/0124914 A1 | 5/2011 | Kirihata et al. |

(Continued)

FOREIGN PATENT DOCUMENTS

| | | |
|---|---|---|
| JP | H02207086 A | 8/1990 |
| JP | 2009504732 A | 2/2009 |
| JP | 2009067777 A | 4/2009 |

(Continued)

OTHER PUBLICATIONS

Crossley et al., "Synthesis and cellular uptake of boron-rich pyrazolopyrimidines: exploitation of the translocator protein for the efficient delivery of boron into human glioma cells" Chem Commun vol. 47 pp. 12179-12181 (Year: 2011).*
English machine translation of JP2012-152647, downloaded from translationportal.epo.org (Year: 2012).*
English machine translation of WO2008/145733, downloaded from translationportal.epo.org (Year: 2008).*
International Preliminary Report on Patentability dated Feb. 7, 2019, during examination of PCT/JP2017/026272.
Harfst et al., Journal of Chromatography A, Aug. 26, 1994, vol. 678, Issue. 1, p. 41-48.
Justus et al., Collection of Czechoslovak Chemical Communications, 2007, vol. 72, No. 12, p. 1740-1754.
Yisgedu et al., Chemistry a European Journal, Feb. 16, 2009, vol. 15, Issue. 9, p. 2190-2199.
Al-Madhoun et al., J. Med. Chem., 2002, 45, 4018-4028.
Cai et al., J. Med. Chem., 1997, 40, 3887-3896.
Compostella et al, Res. Develop. Neutron Capture Ther., 2002, 81-84.

(Continued)

*Primary Examiner* — Eric Olson
(74) *Attorney, Agent, or Firm* — Norton Rose Fulbright US LLP

(57) ABSTRACT

To provide a novel boron-containing compound. A compound represented by the following formula: wherein black circle represents B, white circles represent B—H; —$R^1$ represents —$(CH_2)n$-$X^1$—$R^3$ (n represents an integer of 0 to 6; $X^1$ represents O, S, NH, S—S, O—CO, NHCO or SCO, or does not exist; $R^3$ represents $C_6$-$C_{20}$ alkyl, hydroxy $C_6$-$C_{20}$ alkyl, amino $C_6$-$C_{20}$ alkyl, azido $C_6$-$C_{20}$ alkyl, hydroxycarbonyl $C_6$-$C_{20}$ alkyl, or the like), or a group having a repeating sequence of —$(CH_2)_2$—O— 3 times or more and 10 times or less and having a methyl group or an ethyl group at the end on the oxygen atom side; and —$R^2$ is —$(CH_2)m$-$X^2$—$R^4$ (m represents an integer from 0 to 8; $X^2$ represents O, S, NH, S—S, O—CO, NHCO or SCO, or does not exist; and $R^4$ represents a tumor recognition moiety), or does not exist are prepared and used.

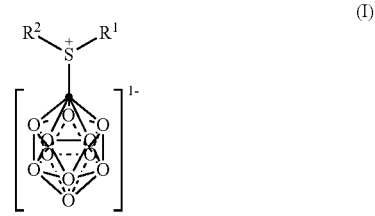

13 Claims, 3 Drawing Sheets

(56) References Cited

U.S. PATENT DOCUMENTS

2011/0184175 A1    7/2011   Kirihata et al.

FOREIGN PATENT DOCUMENTS

| JP | 2012153647 | A | 8/2012 | | |
|----|-----------|---|--------|---|---|
| WO | 2007097065 | A1 | 8/2007 | | |
| WO | WO2008/145733 | | * 12/2008 | ................ | C07F 5/02 |
| WO | 2010/010913 | A1 | 1/2010 | | |
| WO | 2010010912 | A1 | 1/2010 | | |
| WO | 2012/018015 | A1 | 2/2012 | | |

OTHER PUBLICATIONS

Genady et al., Organic & Biomolecular Chemistry, Oct. 7, 2010, Issue 19, pp. 4427-4435, Schemel-2.
Hattori et al., J. Med. Chem., 2012, 55, 6980-6984.
Imamura et al., Bull. Chem. Soc. Jpn., 1997, 70, 3103-3110.
International Search Report dated Sep. 5, 2017 during examination of International Application No. PCT/JP2017/026272.
Japanese Office Action dated Sep. 5, 2017 during the examination of Japanese Patent Application No. 2016-148978 with Machine Translation.
Kahl et al., Progress in Neutron Capture Therapy for Cancer, Plenum Press, New York, 1992, 223.
Kusaka et al., Applied Radiation and Isotopes, 2011, 69, 1768-1770.
Lim et al., Res. Develop. Neutron Capture Ther., 2002, 37-42.
Tjark, W., J. Organomet. Chem., 2000, 614-615, 37-47.
Wyzlic et al., Tetrahedron Lett., 1992, 33, 7489-7490.
Barth: "Boron Neutron Capture Therapy of Cancer: Current Status and Future Prospects", Clinical Cancer Research, vol. 11, No. 11, 2005, pp. 3987-4002.
Extended European Search Report dated Mar. 6, 2020 during prosecution of related European Patent Appl. No. 17834146.7.
Douglass et al: "A versatile monomer for polyelectrolytes via ROMP", Polymer Preprints, vol. 37, No. I, Jan. 1, 1996 (Jan. 1, 1996), p. 634.
Russian Office Action dated May 28, 2020 during the examination of Russian Patent Application No. 2019105302 with translation.
Australia Examination Report dated Oct. 9, 2020 in connection with AU Patent Appl. No. 2017303280.
Taiwan Office Action dated Oct. 5, 2020 in connection with TW Patent Appl. No. 106125522.

* cited by examiner

BORON-CONTAINING COMPOUND

TECHNICAL FIELD

The present invention relates to a boron-containing compound and a method for producing the same. The boron-containing compound of the present invention can be applied to various applications. For example, the boron-containing compound of the present invention is useful as a neutron capture therapy agent for use in boron neutron capture therapy (BNCT).

BACKGROUND ART

Recently, attention has been drawn to a boron neutron capture therapy (BNCT) as a novel cancer treatment method utilizing a radioisotope. The boron neutron capture therapy is a treatment method in which a boron-containing compound containing boron-10 isotope ($^{10}$B) is delivered to cancer cells and the cancer cells are irradiated with a low energy neutron (for example, thermal neutrons), and thus the cancer cells are locally destroyed by a nuclear reaction which arises in the cells. In this treatment method, since it is important to cause a boron-containing compound which contain $^{10}$B to be selectively accumulated by cells of cancerous tissue so as to enhance therapeutic effect, boron-containing compounds which are selectively uptaken by cancer cells have been developed.

Hitherto, some boron-containing compounds in which boron atoms or boron atomic groups are introduced into a basic skeleton have been synthesized as an agent used in BNCT. Examples of an agent used in the actual clinical practice include p-boronophenylalanine (BPA) and mercaptoundecahydrododecaborate (BSH: borocaptate). Among them, BSH is a boron cage (cluster) compound having the lowest toxicity, which is mainly used in the form of a sodium salt for the treatment of brain tumor, and thus utility thereof has been confirmed (see, for example, Non-Patent Documents 1 to 8).

In addition, some compounds modified with BSH have also been proposed (for example, Non-Patent Documents 9 to 10).

PRIOR ART DOCUMENTS

Non-Patent Documents

Non-Patent Document 1: I. M. Wyzlic et al., Tetrahedron Lett., 1992, 33, 7489-7490,
Non-Patent Document 2: W. Tjark, J. Organomet. Chem., 2000, 614-615, 37-47,
Non-Patent Document 3: K. Imamura et al., Bull. Chem. Soc. Jpn., 1997, 70. 3103-3110.
Non-Patent Document 4: A. S. Al-Madhorn et al., J. Med. Chem., 2002, 45, 4018-4028,
Non-Patent Document 5: F. Compostella et al, Res. Develop. Neutron Capture Ther., 2002, 81-84,
Non-Patent Document 6: S. B Kahl et al., Progress in Neutron Capture Therapy for Cancer, Plenum Press, New York 1992, 223,
Non-Patent Document 7: J. Cai et al., J. Med. Chem., 1997, 40, 3887-3896,
Non-Patent Document 8: H. Lim et al., Res. Develop. Neutron Capture Ther., 2002, 37-42
Non-Patent Document 9: S. Kusaka et al., Applied Radiation and Isotopes, 2011, 69, 1768-1770
Non-Patent Document 10: Y. Hattori et al., J. Med. Chem., 2012, 55, 6980-6984

SUMMARY OF THE INVENTION

Problems to be Solved by the Invention

Further development of novel boron-containing compounds selectively uptaken by cancer cells which may be used to carry out BNCT is desired.

The objective of the present invention is to provide a novel boron-containing compound and a method for producing the same, which can be utilized for BNCT and the like.

Means for Solving the Problems

As a result of extensive studies, the present inventors have found that the above objective can be achieved by a boron-containing compound and a method for producing the same as shown below, and have completed the present invention.

That is, the present invention relates to a boron-containing compound represented by the following formula (I) or the following formula (II) or a pharmaceutically acceptable salt thereof.

[Formula 1]

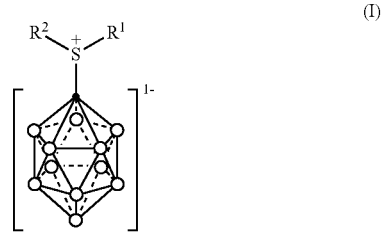

(I)

[Formula 2]

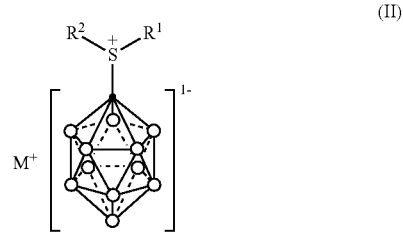

(II)

In the formula (I) or (II), a black circle represents B atom, white circles represent B—H; —$R^1$ represents —$(CH_2)$n-$X^1$—$R^3$ (n represents an integer of 0 to 6; $X^1$ represents O, S, NH, S—S, O—CO, NHCO or SCO, or does not exist; $R^3$ represents $C_6$-$C_{20}$ alkyl, hydroxy $C_6$-$C_{20}$ alkyl, amino $C_6$-$C_{20}$ alkyl, azido $C_6$-$C_2$ alkyl, hydroxycarbonyl $C_6$-$C_{20}$ alkyl, substituted or unsubstituted phenoxy $C_6$-$C_{20}$ alkyl, substituted or unsubstituted phenylthiourea $C_6$-$C_{20}$ alkyl, or a substituted or unsubstituted benzyl group), or a group having a repeating sequence of —$(CH_2)_2$—O— 3 times or more and 10 times or less and having a methyl group or an ethyl group at the end on the oxygen atom side; —$R^2$ is —$(CH_2)$m-$X^2$—$R^4$ (m represents an integer from 0 to 8; $X^2$ represents O, S, NH, S—S, O—CO, NHCO or SCO, or does not exist; $R^4$ represents a tumor recognition moiety selected from the group consisting of amino acids, amino acid amide, 5-aminolevulinic acid, kojic acid or salts thereof, hydroquinone or salts thereof, resveratrol or salts thereof, DPA (dimethylpyrazolopyrimidine acetamide) type TSPO (translocator protein) ligand, caffeic acid or salts thereof, monosaccharides or salts thereof, and nucleic acids or constituents thereof or salts thereof), or does not exist; and M+ represents an alkali metal ion, an ammonium ion or a tetraalkylammonium ion (NR4+), or a tetraphenylphosphonium ion.

The present invention also relates to a method for producing the boron-containing compound of the following formula,

[Formula 4]

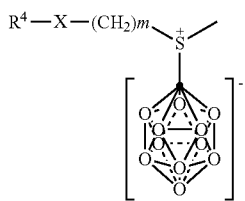

or a pharmaceutically acceptable salt thereof, including the step of reacting a compound represented by

[Formula 3]

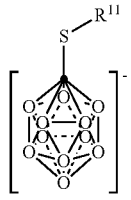

black circle: B, white circle: B—H, (—R11 represents —(CH2)n-X1—R3 (n represents an integer of 0 to 6; X1 represents O, S, NH, S—S, O—CO, NHCO or SCO, or does not exist; R3 represents $C_6$-$C_{20}$ alkyl, hydroxy $C_6$-$C_{20}$ alkyl, amino $C_6$-$C_{20}$ alkyl, azido $C_6$-$C_{20}$ alkyl, hydroxycarbonyl $C_6$-$C_{20}$ alkyl, substituted or unsubstituted phenoxy $C_6$-$C_{20}$ alkyl, substituted or unsubstituted phenylthiourea $C_6$-$C_{20}$ alkyl, or a substituted or unsubstituted benzyl group), or a group having a repeating sequence of —(CH2)2—O— 3 times or more and 10 times or less and having a methyl group or an ethyl group at the end on the oxygen atom side); with R12—(CH2)m-X2—R4 (m represents an integer from 0 to 8; X2 represents O, S, NH, S—S, O—CO, NHCO or SCO, or does not exist; R4 represents a tumor recognition moiety selected from the group consisting of amino acids, amino acid amide, 5-aminolevulinic acid, kojic acid or salts thereof, hydroquinone or salts thereof, resveratrol or salts thereof, DPA (dimethylpyrazolopyrimidine acetamide) type TSPO (translocator protein) ligand, caffeic acid or salts thereof, monosaccharides or salts thereof, and nucleic acids or constituents thereof or salts thereof, and R12 represents a halogen).

The present invention also relates to a method for producing the boron-containing compound,

[Formula 6]

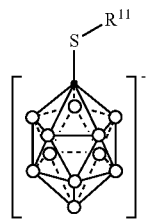

including the step of reacting a compound represented by

[Formula 5]

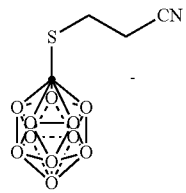

with a compound represented by

R11—R13 wherein R11 represents —(CH2)n-X1—R3 (n represents an integer of 0 to 6; X1 represents O, S, NH, S—S, O—CO, NHCO or SCO, or does not exist; and R3 represents $C_6$-$C_{20}$ alkyl, hydroxy $C_6$-$C_{20}$ alkyl, amino $C_6$-$C_{20}$ alkyl, azido $C_6$-$C_{20}$ alkyl, hydroxycarbonyl $C_6$-$C_{20}$ alkyl, substituted or unsubstituted phenoxy $C_6$-$C_{20}$ alkyl, substituted or unsubstituted phenylthiourea $C_6$-$C_{20}$ alkyl, or a substituted or unsubstituted benzyl group), or a group having a repeating sequence of —(CH2)2—O— 3 times or more and 10 times or less and having a methyl group or an ethyl group at the end on the oxygen atom side; and R13 represents a halogen.

The present invention also relates to a pharmaceutical composition including one or more of the above boron-containing compounds.

Such a pharmaceutical composition may be used for treating cancer with BNCT.

Effect of the Invention

The novel boron-containing compounds and production method of the present invention can be suitably used, in particular, for BNCT.

MODE FOR CARRYING OUT THE INVENTION

Figure 1:
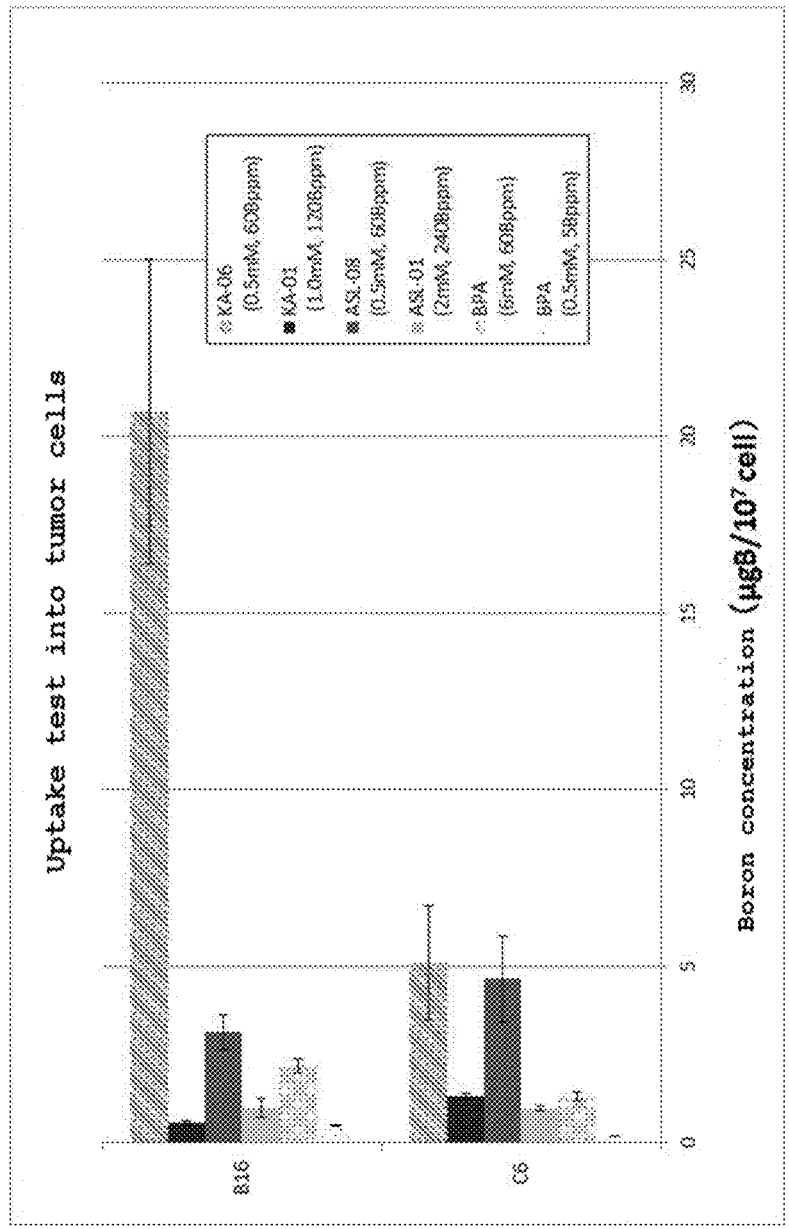
FIG. 1 is a graph showing the results of an uptake test on a boron-containing compound of the present invention and other compounds into tumor cells.

The present invention relates to a boron-containing compound represented by the following chemical formula (I).

[Formula 7]

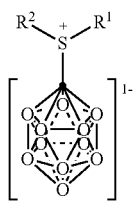

(I)

The present invention also relates to a salt of a boron-containing compound represented by the following chemical formula (II).

[Formula 8]

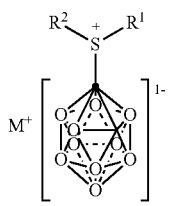

(II)

In the formula (I) or (II), a black circle represents B atom, white circles represent B—H; —$R^1$ represents —$(CH_2)$n-$X^1$—$R^3$ (n represents an integer of 0 to 6; $X^1$ represents O, S, NH, S—S, O—CO, NHCO or SCO, or does not exist; $R^3$ represents $C_6$-$C_{20}$ alkyl, hydroxy $C_6$-$C_{20}$ alkyl, amino $C_6$-$C_{20}$ alkyl, azido $C_6$-$C_{20}$ alkyl, hydroxycarbonyl $C_6$-$C_{20}$ alkyl, substituted or unsubstituted phenoxy $C_6$-$C_{20}$ alkyl, substituted or unsubstituted phenylthiourea $C_6$-$C_{20}$ alkyl, or a substituted or unsubstituted benzyl group), or a group having a repeating sequence of —$(CH_2)_2$—O— 3 times or more and 10 times or less and having a methyl group or an ethyl group at the end on the oxygen atom side. Here, the left end portion of —$(CH_2)$n-$X^1$—$R^3$ of $R^1$ indicates the S atom side in the formula (I).

—$R^2$ is —$(CH_2)$m-$X^2$—$R^4$ (m represents an integer from 0 to 8; $X^2$ represents O, S, NH, S—S, O—CO, NHCO or SCO, or does not exist; $R^4$ represents a tumor recognition moiety selected from the group consisting of amino acids, amino acid amide, 5-aminolevulinic acid, kojic acid or salts thereof, hydroquinone or salts thereof, resveratrol or salts thereof, DPA (dimethylpyrazolopyrimidine acetamide) type TSPO (translocator protein) ligand, caffeic acid or salts thereof, monosaccharides or salts thereof, and nucleic acids or constituents thereof or salts thereof), or does not exist.

Here, $M^+$ represents a monoatomic cation, a polyatomic cation, or a complex cation.

When —$R^2$ does not exist, $S^+$ in the formula is S.

Here, the part corresponding to BSH of the compound is a compound having an icosahedral boron cluster structure including boron, hydrogen, and sulfur atoms. BSH, having a so-called three-center bond structure in which three boron atoms have two electrons in common, has a specific structure in which electrons are localized, and has a volume that is larger than that of a benzene ring despite the fact that the BSH is an inorganic compound of low molecular weight. The part corresponding to BSH is sometimes herein simply referred to as $S^{10}B_{12}H_{11}$.

As used herein, the substitution in the term "substituted or unsubstituted phenyl", "substituted or unsubstituted phenoxy $C_6$ to $C_{20}$ alkyl" or "substituted or unsubstituted benzyl" refers to that the phenyl group may have the same or different substituents at any one or two positions thereof. Although not limited, such substituent refers to being substituted with preferably a $C_{1-6}$ alkyl group, a $C_{1-6}$ alkoxy group, a hydroxy group, an amino group, a di $C_{1-6}$ alkylamino group, a nitro group, an azido group, a thiol group, a dihydroxyboryl acid (boric acid group), a carboxyl group, a cyano group, a trifluoromethyl group, or halogen. Here, preferred examples of the $C_{1-6}$ alkyl group include a methyl group, an ethyl group, a propyl group, a butyl group, and the like. The $C_{1-6}$ alkoxy group is particularly preferably a methoxy group, the di $C_{1-6}$ alkylamino group is particularly preferably a methylamino group, and the halogen is particularly preferably fluorine.

As used herein, the term "substituted or unsubstituted phenylthiourea $C_6$-$C_{20}$ alkyl" refers to that the phenyl group may have the same or different substituents at any one or two positions thereof. The substituent is preferably, but not limited to, fluorescein, coumarin sulfate, boron dipyrromethene (BODIPY), or rhodamine.

As used herein, $C_6$-$C_{20}$ alkyl may be either branched or linear or cyclic alkyl. Although not limited, examples thereof include heptyl, octyl, nonyl, decyl, icosyl, isooctyl, $C_6$-$C_{16}$ cycloalkyl, and the like. Particularly preferred is linear $C_8$-$C_{16}$ alkyl.

As used herein, examples of the amino acids in $R^4$ include essential amino acids (including D- and L-forms), BPA (p-boronophenylalanine), and a cyclo ring-containing amino acid. Also, the amino acid amide in $R^4$ has a structure in which the carboxyl group among these amino acids is replaced by CONH. Here, the cyclo ring in the cyclo ring-containing amino acid is preferably a $C_{3-6}$ cyclo ring. Specific examples of the cyclo ring-containing amino acid include aminocyclobutanoic acid. The essential amino acid is alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine.

As used herein, the monosaccharides typically refer to aldose or ketose. The monosaccharides used in the present invention may be any one of triose, tetrose, pentose, and hexose. More specifically, examples of these monosaccharides include aldoses such as glyceraldehyde, erythrose, threose, ribose, lyxose, xylose, arabinose, allose, talose, gulose, glucose, altrose, mannose, galactose, or idose; and ketoses such as dihydroxyacetone, erythrulose, xylulose, ribulose, psicose, fructose, sorbose, or tagatose.

As used herein, it is preferable that 5-aminolevulinic acid is either $NH_2$—$CH_2$—CO—$(CH_2)_2$—COO— or $NH_2$—$(CH_2)$—CO—$(CH_2)_2$—CO—NH—.

As used herein, DPA (dimethylpyrazolopyrimidine acetamide) type TSPO (translocator protein) ligand refers to N,N-diethyl-2-[4-(2-hydroxyphenyl)]-5,7-dimethylpyrazolo[1,5-α]pyrimidine-3-acetamide (DPA) type TSPO and the like, and has, for example, the following structure, although not limited thereto.

[Formula 9]

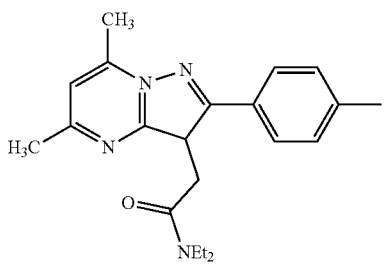

As used herein, the nucleic acids or constituents thereof refer to preferably a sequence of one nucleotide or two or more nucleotides. ATP, GTP, CTP, UTP, dATP, dGTP, dCTP, or dTTP, or a combination of two or more thereof is included.

$M^+$ represents a monoatomic cation, a polyatomic cation, or a complex cation, and examples thereof include alkali metal ions such as sodium ion and potassium ion; alkaline earth metal ions such as calcium ion and magnesium ion; and inorganic bases such as aluminum ion and ammonium ion. Furthermore, for example, organic bases such as trimethylamine, triethylamine, pyridine, picoline, ethanolamine, diethanolamine, triethanolamine, dicyclohexylamine, N,N'-dibenzylethylenediamine, and sulfonium ion can also be used. Preferred examples of M include, but are not limited to, alkali metal ions, ammonium ions or tetraalkylammonium ions ($NR^{4+}$), or tetraphenylphosphonium ions.

As used herein, when referring to a salt of a nucleic acid or a constituent thereof, caffeic acid, kojic acid, hydroquinone, resveratrol or monosaccharides, it is preferably a pharmaceutically acceptable salt. Examples of the pharmaceutically acceptable salt include salts with an inorganic base, salts with an organic base, salts with an inorganic acid, salts with an organic acid, salts with a basic or acidic amino acid, and the like. Preferred examples of the salts with an inorganic base include, for example, alkali metal salts such as a sodium salt and a potassium salt; alkaline earth metal salts such as a calcium salt and a magnesium salt; an aluminum salt, an ammonium salt and the like. Preferred examples of the salts with an organic base include, for example, salts with trimethylamine, triethylamine, pyridine, picoline, ethanolamine, diethanolamine, triethanolamine, dicyclohexylamine, N,N'-dibenzylethylenediamine, and the like. Preferred examples of the salts with an inorganic acid include, for example, salts with hydrochloric acid, hydrobromic acid, nitric acid, sulfuric acid, phosphoric acid, and the like. Preferred examples of the salts with an organic acid include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like. Preferred examples of the salts with a basic amino acid include, for example, salts with arginine, lysine, ornithine and the like, and preferred examples of the salts with an acidic amino acid include, for example, salts with aspartic acid, glutamic acid and the like.

Here, according to a preferred embodiment, —$R^1$ is —$(CH_2)$ n-$X^1$—$R^3$ (n represents an integer of 1 to 4; $X^1$ represents O, S, NH, S—S, O—CO, NHCO or SCO; and $R^3$ represents $C_6$-$C_{20}$ alkyl); and $M^+$ is an alkali metal ion, an ammonium ion or a tetraalkylammonium ion ($NR^{4+}$), or a tetraphenylphosphonium ion.

In another preferred embodiment, —$R^2$ is —$(CH_2)$m-$X^2$—$R^4$ (m represents an integer from 0 to 8; $X^2$ represents O, S, NH, S—S, O—CO, NHCO or SCO, or does not exist; and —$R^4$ represents a kojic acid represented by

[Formula 10]

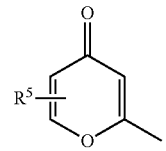

wherein $R^5$ is a hydroxyl group or a salt thereof). In the present invention, —in the chemical formula represents a bond of a single bond and does not mean a methyl group.

In yet another embodiment, —$R^2$ is —$(CH_2)$m-$X^2$—$R^4$ (m represents an integer from 0 to 8; $X^2$ represents O, S, NH, S—S, O—CO, NHCO or SCO, or does not exist; and —$R^4$ is

[Formula 11]

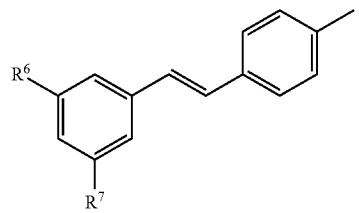

wherein $R^6$ and $R^7$ may be the same or different, and represent a group selected from a hydroxyl group and salts thereof).

In another embodiment, —$R^2$ is —$(CH_2)$m-$X^2$—$R^4$ (m represents an integer from 0 to 8; $X^2$ represents O, S, NH, S—S, O—CO, NHCO or SCO, or does not exist; and —$R^4$ is a compound represented by either

[Formula 12]

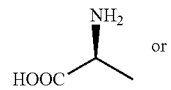

or

[Formula 13]

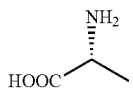

or a salt thereof.

In another embodiment, —$R^2$ is —$(CH_2)$m-$X^2$—$R^4$ (m represents an integer from 0 to 8; $X^2$ represents O, S, NH, S—S, O—CO, NHCO or SCO, or does not exist; and —$R^4$ is any one group selected from groups represented by

[Formula 14]

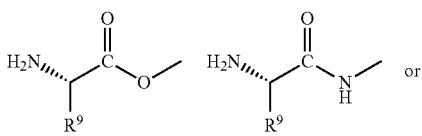 or

[Formula 15]

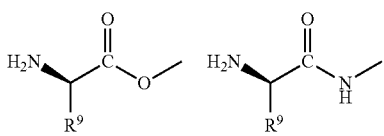

wherein $R^9$ is hydrogen, methyl, isobutyl, 1-propyl, isopropyl, tert-butyl, ethyl, carbonylmethyl, 2-carbonylethyl, hydroxymethyl, hydroxy, mercaptomethyl, methylthioethyl, 2-amino-2-oxoethyl, 3-amino-3-oxopropyl, substituted or unsubstituted benzyl, 4-hydroxybenzyl, 3-aminopropyl, 4-aminobutyl, 3-guanidinopropyl, indolylmethyl, imidazolemethyl, substituted or unsubstituted phenyl, 1-hydroxyethyl or para-boronophenyl, and salts thereof).

In another embodiment, —$R^2$ is —$(CH_2)m$-$X^2$—$R^4$ (m represents an integer from 0 to 8; $X^2$ represents O, S, NH, S—S, O—CO, NHCO or SCO, or does not exist; and —$R^4$ is any one group selected from groups represented by

[Formula 16]

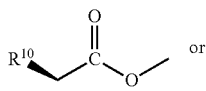 or

[Formula 17]

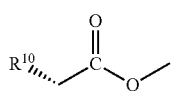

wherein $R^{10}$ represents

[Formula 18]

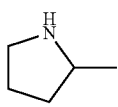

and salts thereof.

In another embodiment, —$R^2$ is —$(CH_2)m$-$X^2$—$R^4$ (m represents an integer from 0 to 8; $X^2$ represents O, S, NH, S—S, O—CO, NHCO or SCO, or does not exist; and —$R^4$ is any one group selected from groups represented by

[Formula 19]

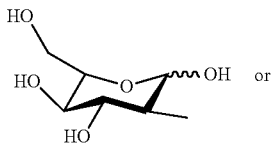 or

[Formula 20]

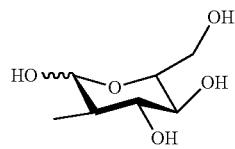

and salts thereof.

In another embodiment, $R^2$ does not exist.

Hereinafter, a method for producing the boron-containing compound represented by the chemical formula (I) of the present invention will be described.

In the method for producing the boron-containing compound (I) of the present invention, cyanoethyl BSH represented by the general formula (1a):

[Formula 21]

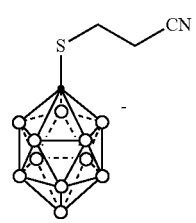

is used as a raw material. These BSH compounds can be synthesized, but not limited to, according to the method known from the literatures (for example, Gabel, D.; Moller, D.; Harfst, S.; Rosler, J.; Ketz, H.; Inorg. Chem. 1993, 32, 2276-2278). That is, this method includes reacting BSH and β-bromopropionitrile in acetonitrile, and then treating the product with tetramethyl ammonium hydroxide and the like, thereby to obtain an objective cyanoethyl BSH compound.

The boron-containing compound of the present invention can be produced by reacting the cyanoethyl BSH (1a) with a compound represented by the general formula (2a):

$$R^{11}—R^{13} \qquad (2a)$$

wherein $R^{11}$ represents —$(CH_2)n$-$X^1$—$R^3$ (n represents an integer of 0 to 6; $X^1$ represents O, S, NH, S—S, O—CO, NHCO or SCO, or does not exist; and $R^3$ represents $C_6$-$C_{20}$ alkyl, hydroxy $C_6$-$C_{20}$ alkyl, amino $C_6$-$C_{20}$ alkyl, azido $C_6$-$C_{20}$ alkyl, hydroxycarbonyl $C_6$-$C_{20}$ alkyl, substituted or unsubstituted phenoxy $C_6$-$C_{20}$ alkyl, substituted or unsubstituted phenylthiourea $C_6$-$C_{20}$ alkyl, or a substituted or unsubstituted benzyl group), or a group having a repeating sequence of —$(CH_2)_2$—O— 3 times or more and 10 times or less and having a methyl group or an ethyl group at the end on the oxygen atom side; and $R^{13}$ is a halogen.

The reaction conditions here are not limited, but are preferably a reaction temperature of 80° C. or more, and a reaction time of 12 hours or more and 72 hours or less. The solvent to be used is preferably dimethylformamide, dimethylsulfoxide, acetonitrile, or the like.

Here, as the chemical formula (2a), a commercially available product can be used, or it can be synthesized and used. The production method of these compounds is not limited, but as an example, the synthetic route for 6-bromohexyloxybenzene will be shown.

[Formula 22]

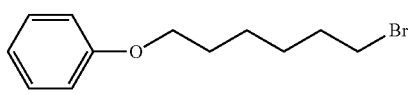

The present compound can be produced by dissolving phenol in acetonitrile and reacting with dibromohexane, in the presence of any one selected from potassium carbonate, sodium carbonate, sodium hydroxide, and potassium hydroxide.

Other than acetonitrile, acetone, dimethylformamide, dimethylsulfoxide, tetrahydrofuran, 1,4-dioxane and the like can be used as a solvent in the above reaction. Among them, acetonitrile and acetone are preferably used.

The reaction conditions here are not limited, but the reaction is preferably performed at a temperature of 60° C. or more and 120° C. or less for 3 hours and more.

Further, by appropriately changing the chain length of the dibromoalkane, a compound having an arbitrary alkyl chain length can be obtained.

In each step, a subsequent step is done after appropriate neutralization and purification steps have been applied. Each product obtained in the each step may be isolated and purified, or may be subjected to the subsequent step as it is. The isolation and purification means include washing, extraction, recrystallization methods, various chromatographies, and the like. In each product in the each step, these isolation and purification means can also be used alone, or in appropriate combination of two or more kinds of them.

In the present invention, it is also possible to produce a compound group having a higher tumor recognition ability. Although not limited, as a method for producing such a compound, there are the following methods. That is, such a method includes the step of reacting a compound represented by the following chemical formula (III)

[Formula 23]

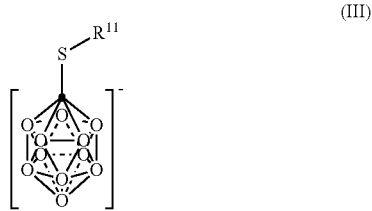

(III)

black circle: B, white circle: B—H,
($R^{11}$ represents —$(CH_2)$n-$X^1$—$R^3$ (n represents an integer of 0 to 6; $X^1$ represents O, S, NH, S—S, O—CO, NHCO or SCO, or does not exist; $R^3$ represents $C_6$-$C_{20}$ alkyl, hydroxy $C_6$-$C_{20}$ alkyl, amino $C_6$-$C_{20}$ alkyl, azido $C_6$-$C_{20}$ alkyl, hydroxycarbonyl $C_6$-$C_{20}$ alkyl, substituted or unsubstituted phenoxy $C_6$-$C_{20}$ alkyl, substituted or unsubstituted phenylthiourea $C_6$-$C_{20}$ alkyl, or a substituted or unsubstituted benzyl group), or a group having a repeating sequence of —$(CH_2)_2$—O— 3 times or more and 10 times or less and having a methyl group or an ethyl group at the end on the oxygen atom side); with $R^{12}$—$(CH_2)$m-$X^2$—$R^4$ (m represents an integer from 0 to 8; $X^2$ represents O, S, NH, S—S, O—CO, NHCO or SCO, or does not exist; $R^4$ represents a tumor recognition moiety selected from the group consisting of amino acids, kojic acid or salts thereof, hydroquinone or salts thereof, resveratrol or salts thereof, benzodiazepine type TSPO (translocator protein) ligand, monosaccharides or salts thereof, and nucleic acids; and $R^{12}$ represents a halogen).

In the above production method, it is possible to dissolve the compound of the chemical formula (III) in acetonitrile, and add the compound represented by $R^{12}$—$(CH_2)$m-$X_2$—$R^4$ thereto to react the mixture at 70° C. or more and 140° C. or less for 12 hours or more.

Other than acetonitrile, dimethylformamide), dimethylsulfoxide, methanol, ethanol and the like can also be used as the solvent in the above reaction. Among them, acetonitrile and dimethylformamide are preferably used.

In the above reaction, the type of the salt of the chemical formula (III) is not particularly limited, but a sodium salt, a tetramethylammonium salt or the like is preferable. In addition, halogen is not particularly limited, but Br is preferably used.

Such a compound can be suitably used as it is, or used in the form of a pharmaceutically acceptable salt, or used in the form of a pharmaceutical preparation known to a person ordinarily skilled in the art by mixing it with a pharmaceutically acceptable carrier, or used in the form of a BSH-enclosed viral envelope vector and the like in a boron neutron capture therapy (BNCT). That is, it can be used as a pharmaceutical composition or as a cancer therapeutic agent.

The treatment is performed via any appropriate route of administration by administering an agent containing a compound of the present invention using a method in which the compound is accumulated at the target site. The compound of the present invention is preferably concentrated in tumor. The pharmaceutical preparation containing the compound can be administered at a time, or can be sequentially administered. Administration of the pharmaceutical preparation can be repeated as necessary. If desired, after removing the tumor to a surgically possible extent, the remaining tumor can also be destroyed using a pharmaceutical preparation of the present invention.

A treatment with the boron-containing compound pharmaceutical preparation of the present invention is performed via any appropriate route of administration by administering it using a method in which the boron-containing compound is accumulated in the target tumor.

The boron-containing compound is preferably concentrated to the tumor before irradiation with radiation, and a tumor/blood ratio before irradiation with radiation is advantageously about 2:1 or at least 1.5:1. In BNCT, it is important to have a boron concentration ratio between the tumor and its surrounding normal tissues, and a compound in which boron is introduced into the structure selectively accumulating in the tumor of the present invention is very useful. This is because a boron concentration ratio occurs between the tumor and the surrounding normal tissues and it is possible to selectively destroy the tumor while reducing the damage of surrounding normal tissues. On the other hand, in order to make BNCT successful, it is necessary to accumulate about 20 ppm of boron in the tumor, and it can be achieved by adjusting the dose. The boron-containing compound can be administered at a time, or can be sequentially administered. After the compound is desirably accumulated in the tumor, the site is irradiated with an effective amount of low energy neutrons. The site can be irradiated through the skin, or the site can be completely or partially exposed before irradiation. Administration of the boron-containing compound and the subsequent irradiation can be repeated as necessary. If desired, after removing the tumor to a surgically possible extent, the remaining tumor is destroyed using the boron-containing compound of the present invention. In another embodiment, a proper amount of the boron-containing compound is administered to patients, followed by irradiation with an effective amount of $^{252}$californium which is a naturally occurring neutron radiation substance. It is preferred that $^{252}$californium is inserted into the tumor and then removed within a proper time.

Here, the type of tumor is not particularly limited, but a brain tumor including glioblastoma and malignant glioma and the like, malignant melanoma, breast cancer, or prostate cancer and the like can be particularly suitable subjects. In addition, epithelial cell carcinoma such as lung cancer, uterus cancer, kidney cancer and liver cancer, various sarcomas and the like can be targeted.

In order to administer the boron-containing compound of the present invention, the boron-containing compound may be administered to patients by mixing with proper excipients, adjuvants and/or pharmaceutically acceptable carriers, alone or in combination with other agents. The carriers which can be particularly preferably used are, but are not limited to, pharmaceutically inert aqueous carriers. Such carriers include physiological saline, buffered physiological saline, dextrose, water, and the like. In an embodiment of the present invention, the pharmaceutically acceptable carriers are pharmaceutically inactive.

The boron-containing compound of the present invention may be administered orally and parenterally. In the case of parenteral administration, it may be administered intraarterially (for example, via carotid artery), intramuscularly, subcutaneously, intramedullary, intrathecally, intraventricularly, intravenously, intraperitoneally, or intranasally.

The pharmaceutical preparation may be formulated into any form such as powders, granules, fine granules, dry syrups, tablets, capsules, injections, and liquids and solutions. In addition, depending on the dosage form, the pharmaceutical preparation can be prepared by appropriately mixing with, or diluting and dissolving together with pharmaceutical additives such as proper excipients; disintegrators; binders; lubricants; diluents; buffer buffers such as phosphoric acid, citric acid, succinic acid, acetic acid and other organic acids, or salts thereof; isotonizing agents; antiseptics; humectants; emulsifiers; dispersing agents; stabilizers; solubilizers; antioxidants such as ascorbic acid; low molecular (less than about 10 residues) polypeptides (for example, polyarginine or tripeptides); proteins (for example, serum albumin, gelatin, or immunoglobulin); hydrophilic polymers (for example, polyvinylpyrrolidone); amino acids (for example, glycine, glutamic acid, aspartic acid, or arginine); monosaccharides, disaccharides and other carbohydrates (including cellulose or derivatives thereof, glucose, mannose, or dextrin); chelating agents (for example, EDTA); sugar alcohols (for example, mannitol or sorbitol); counter ions (for example, sodium); and/or nonionic surfactants (for example, polysorbate, poloxamer), according to the pharmaceutically known techniques. Such a substance, which enhances isotonicity and chemical stability, is non-toxic to the recipient at the dosages and concentrations used. Particularly preferred for the pharmaceutical preparation are injections prepared with an aqueous carrier.

Techniques for formulation and administration are described, for example, in the latest edition of the Japanese Pharmacopoeia and its latest supplement, and in the final version of "REMINGTON'S PHARMACEUTICAL SCIENCES" (Maack Publishing Co., Easton, Pa.).

A pharmaceutical preparation of the boron-containing compound of the present invention is an agent contained in an amount effective for the objective agent to achieve the intended purpose, and the "therapeutically effective amount" or "pharmacologically effective amount" is well recognized by a person ordinarily skilled in the art, and refers to an amount of an agent effective to produce a pharmacological result. Determination of a therapeutically effective dose is well known to a person ordinarily skilled in the art.

The therapeutically effective amount refers to an amount of the agent to alleviate the disease state by the administration. The therapeutic effect and toxicity of such compounds may be determined by standard pharmaceutical procedures in cell cultures or experimental animals. The dose is preferably in the range of circulating concentrations that include the $ED_{50}$ with little or no toxicity. This dose varies within this range depending on the dosage form used, sensitivity of patients, and administration route. As an example, the dose of a composite is appropriately chosen depending on the age or other conditions of patients, the kind of diseases, the kind of composites to be used and the like. Preferred daily dose of the compound of the chemical formula (I) is 0.01 to 1,000 mg per 1 kg of the weight of the mammal to be treated. In humans, the preferred daily dose of the compound of the chemical formula (I) is 0.01 to 800 mg, and more preferably 1 to 600 mg, per 1 kg of the weight.

The present invention relates to a pharmaceutical composition containing one or more boron-containing compounds represented by the chemical formula (I) or (II) or pharmaceutically acceptable salts thereof. That is, the pharmaceutical composition of the present invention contains one or more boron-containing compounds represented by the chemical formula (I) or (II) or pharmaceutically acceptable salts thereof.

The present invention relates to the use of one or more boron-containing compounds represented by the chemical formula (I) or (II) or pharmaceutically acceptable salts thereof for producing a medicament for treating cancer. Here, it is preferable that cancer treatment is performed using BNCT.

The present invention relates to the use of one or more boron-containing compounds represented by the chemical formula (I) or (II) or pharmaceutically acceptable salts thereof for producing a medicament for treating cancer by BNCT.

Hereinafter, specific examples of the production of the boron-containing compound of the present invention will be described by way of embodiment of examples, but the present invention is not limited thereto.

EXAMPLES

In the following examples, analysis and isolation and purification of compounds were performed using the following models and reagents. •NMR spectrum: JEOL JMTC-400/54/SS 400 MHz (manufactured by JEOL Ltd.). Unless otherwise specified, TMS was used as an internal standard. The following chemical shift was expressed by the δ value. •Silica gel for column chromatography: BW-200 (manufactured by FUJI SILYSIA CHEMICAL LTD.) •Melting point: Measured using BUCHI Melting point B-545•IR: Measured using JASCO FT/IR-460 plus.

Example 1-1

Production of S-n-Octyl-Thioundecahydro-Closo-Dodecaborate Disodium Salt

S-(2-Cyanoethyl)-thioundecahydro-closo-dodecaborate 2 tetramethylammonium salt (250 mg, 0.685 mmol) was dissolved in acetonitrile (10 mL), and 1-bromooctane (142 μL, 0.822 mmol) was added thereto, then the mixture was heated under reflux for 24 hours. After concentrating the reaction mixture to dryness, acetone (100 mL) was added thereto and the insoluble materials were removed by filtration. 25% tetramethylammonium hydroxide/methanol (250 mg, 0.685 mmol) was added to the filtrate, and the resulting precipitate was collected by filtration and washed with acetone. The obtained colorless solid was dissolved in $H_2O$ (100 mL), amberlite IR120 ($H^+$) (5.0 mL) was added thereto, and the mixture was allowed to stand for 30 minutes. The reaction mixture was filtered, and the filtrate was neutralized with 1 N NaOH and then concentrated to dryness to obtain the objective compound (159 mg, 72.0%) as a colorless amorphous solid. $^1$H NMR (DMSO-$d_6$): 0.25-1.65 (m, 26H), 2.08-2.09 (m, 2H), 2.19-2.23 (m, 2H)

In the same manner, the compounds shown in the following Table 1 were synthesized.

TABLE 1

|  | Compound name | Structural formula | $^1$H NMR |
|---|---|---|---|
| Reference Example | ABS01 | $CH_3$<br>\|<br>$S^{10}B_{12}H_{11}Na_2$ | 1H NMR (DMSO-d6): 0.43-1.44 (m, 11H), 1.69 (s, 3H). |
| Reference Example | ABS02 | $C_4H_9$<br>\|<br>$S^{10}B_{12}H_{11}Na_2$ | 1H NMR (DMSO-d6): 0.43-1.44 (m, 18H), 2.23 (t, 2H, J = 7.6 Hz). |
| Example 1-2 | ABS03 | $C_6H_{13}$<br>\|<br>$S^{10}B_{12}H_{11}Na_2$ | 1H NMR (DMSO-d6): 0.42-1.44 (m, 22H), 2.08-2.09 (m, 2H), 2.21 (t, 2H, J = 7.6 Hz) |
| Example 1-3 | ABS04 | $C_8H_{17}$<br>\|<br>$S^{10}B_{12}H_{11}Na_2$ | 1H NMR (DMSO-d6): 0.42-1.44 (m, 26H), 2.08-2.09 (m, 2H), 2.21 (t, 2H, J = 7.6 Hz) |
| Example 1-4 | ABS05 | $C_{10}H_{21}$<br>\|<br>$S^{10}B_{12}H_{11}Na_2$ | 1H NMR (DMSO-d6): 0.42-1.44 (m, 30H), 2.08-2.09 (m, 2H), 2.20 (t, 2H, J = 7.6 Hz) |
| Example 1-5 | ABS06 | $C_{12}H_{25}$<br>\|<br>$S^{10}B_{12}H_{11}Na_2$ | 1H NMR (DMSO-d6): 0.42-1.44 (m, 34H), 2.08-2.09 (m, 2H), 2.20 (t, 2H, J = 7.6 Hz) |
| Example 1-6 | ABS07 | $C_{14}H_{29}$<br>\|<br>$S^{10}B_{12}H_{11}Na_2$ | 1H NMR (DMSO-d6): 0.42-1.44 (m, 38H), 2.08-2.09 (m, 2H), 2.21 (t, 2H, J = 7.6 Hz) |
| Example 1-7 | ABS08 | $C_{16}H_{33}$<br>\|<br>$S^{10}B_{12}H_{11}Na_2$ | 1H NMR (DMSO-d6): 0.42-1.44 (m, 42H), 2.08-2.09 (m, 2H), 2.21 (t, 2H, J = 7.6 Hz) |
| Example 1-8 | ABS09 | $C_{18}H_{37}$<br>\|<br>$S^{10}B_{12}H_{11}Na_2$ | 1H NMR (DMSO-d6): 0.42-1.44 (m, 46H), 2.08-2.09 (m, 2H), 2.21 (t, 2H, J = 7.6 Hz) |
| Example 1-9 | ABS10 | $C_{20}H_{41}$<br>\|<br>$S^{10}B_{12}H_{11}Na_2$ | 1H NMR (DMSO-d6): 0.42-1.44 (m, 50H), 2.08-2.09 (m, 2H), 2.21 (t, 2H, J = 7.6 Hz) |
| Example 1-10 | ABS11 | $C_8H_{16}OH$<br>\|<br>$S^{10}B_{12}H_{11}Na_2$ | 1H NMR (CD3CN): 0.45-1.60 (brm, 23H), 2.39 (t, 2H, J = 7.2 Hz), 3.09 (t, 2H, J = 7.2 Hz Hz) |
| Example 1-11 | ABS12 | $C_8H_{16}NH_2$<br>\|<br>$S^{10}B_{12}H_{11}Na_2$ | 1H NMR (DMSO-d6): 0.45-1.44 (brm, 23H), 1.51 (t, 2H, J = 9.2 Hz), 2.21 (t, 2H, J = 9.2 Hz) |
| Example 1-12 | ABS13 | $C_8H_{16}N_3$<br>\|<br>$S^{10}B_{12}H_{11}Na_2$ | 1H NMR (CD3CN): 0.45-1.60 (brm, 23H), 2.39 (t, 2H, J = 7.2 Hz), 3.27 (t, 2H, J = 7.2 Hz Hz) |

TABLE 1-continued

| Compound name | | Structural formula | $^1$H NMR |
|---|---|---|---|
| Reference Example | ABS14 | (isobutyl group)—$S^{10}B_{12}H_{11}Na_2$ | 1H NMR (CD$_3$CN): 0.45-1.55 (brm, 17H), 1.63-1.70 (m, 1H), 2.24 (d, 2H, J = 6.4 Hz) |
| Example 1-14 | ABS15 | (HO)$_2$B—C$_6$H$_4$—O—(CH$_2$)$_6$—$S^{10}B_{12}H_{11}Na_2$ | $^1$H NMR (D$_2$O): 0.85-1.78 (m, 21H), 2.15-2.26 (m, 2H), 3.95 (t, 2H, J = 6.4), 6.90 (d, 2H, J = 8.0 Hz), 7.63 (d, 2H, J = 8.0 Hz). |
| Example 1-15 | ABS16 | CH$_3$O—(CH$_2$CH$_2$O)$_3$—(CH$_2$)$_n$—$S^{10}B_{12}H_{11}Na_2$ | 1H NMR (CD$_3$CN): 0.45-1.60 (brm, 11H), 2.55 (t, 2H, J = 5.6 Hz), 3.34 (s, 3H), 3.48-3.60 (m, 14H,) |
| Example 1-16 | ABS17 | (fluorescein-phenyl-NH—C(=S)—NH—(CH$_2$)$_n$—$S^{10}B_{12}H_{11}Na_2$) | $^1$H NMR (D$_2$O): 0.56-1.78 (m, 23H), 2.34-2.49 (m, 2H), 3.14-3.59 (m, 2H), 6.40 (br, 1H), 6.56-6.65 (m, 5H), 6.95-7.35 (m, 6H), 7.49 (br, 1H), 7.65 (s, 1H). |
| Example 1-17 | ABS18 | (cycloheptyl)—$S^{10}B_{12}H_{11}Na_2$ | 1H NMR (DMSO-d6): 0.42-1.59 (m, 23H), 1.91-1.98 (m, 2H), 2.06-2.77 (m, 1H) |

(Example 2-1) Production of (S-((3-Amino-3-Hydroxycarbonylbutyl)octyl)-λ$^3$-Sulfanyl)Undecahydro-Closo-Dodecaborate Sodium Salt S-n-Octyl-thioundecahydro-closo-dodecaborate disodium salt (122 mg, 0.338 mmol) obtained in Example 1 was dissolved in acetonitrile (10 mL), and (S)-(+)-2-amino-4-bromobutanoic acid bromate (119 mg, 0.453 mmol) was added thereto, then the mixture was heated under reflux for 24 hours. After concentrating the reaction mixture to dryness, acetone (100 mL) was added thereto and the insoluble materials were removed by filtration. After concentrating the filtrate, the resulting mixture was purified by ODS column chromatography (H$_2$O-80% H$_2$O/MeCN) and freeze-dried to obtain the objective compound (110 mg, 81.3%) as a colorless powder. $^1$H NMR (D$_2$O): 0.55-1.65 (m, 24H), 2.20-2.50 (m, 1H), 3.85-3.29 (m, 4H), 3.79-3.87 (m, 1H).

In the same manner, the compounds shown in Tables 2 to 4 were synthesized.

TABLE 2

| Compound name | | Structural formula | $^1$H NMR |
|---|---|---|---|
| Reference Example | ASL01 | Na$_2$H$_{11}$$^{10}$B$_{12}$S—(CH$_2$)$_2$—CH(NH$_2$)—CO$_2$H | |

TABLE 2-continued

| | Compound name | Structural formula | $^1$H NMR |
|---|---|---|---|
| Reference Example | ASL02 | $NaH_{11}{}^{10}B_{12}S$–(CH linked to $NH_2$, $CO_2H$, and branch to $NH_2$, $HO_2C$) | 1H NMR (D$_2$O): 0.75-1.80 (br, 11H), 2.21-2.28 (m, 4H), 2.97-3.26 (m, 4H), 3.69-3.76 (m, 2H) |
| Reference Example | ASL03 | $NaH_{11}{}^{10}B_{12}S$–chain with $NH_2$, $CO_2H$, CN | |
| Reference Example | ASL04 | $NaH_{11}{}^{10}B_{12}S$–chain with $NH_2$, $CO_2H$, methyl | 1H NMR (D$_2$O): 0.81-1.80 (m, 11H), 2.19-2.31 (m, 2H), 2.52 (s, 3H), 2.85-3.22 (m, 2H), 3.70-3.78 (m, 1H). |
| Reference Example | ASL05 | $NaH_{11}{}^{10}B_{12}S$–chain with $NH_2$, $CO_2H$, propyl | 1H NMR (D$_2$O): 0.65-1.75 (m, 18H), 2.29-2.42 (m, 2H), 2.93-3.26 (m, 4H), 3.87-3.93 (m, 1H). |
| Reference Example | ASL06 | $NaH_{11}{}^{10}B_{12}S$–chain with $NH_2$, $CO_2Et$, isobutyl | 1H NMR (D$_2$O): 0.79-1.82 (m, 17H), 1.99-2.10 (m, 1H), 2.28-2.40 (m, 2H), 2.84 (dd, 1H, J = 12.8 Hz, 7.2 Hz,), 2.94-3.03 (m, 2H), 3.04-3.27 (m, 2H), 3.79-3.87 (m, 1H). |
| Example 2-2 | ASL07 | $NaH_{11}{}^{10}B_{12}S$–chain with $NH_2$, $CO_2H$, $C_6H_{13}$ | 1H NMR (D$_2$O): 0.65-1.75 (m, 20H), 2.25-2.45 (m, 2H), 2.96-3.29 (m, 4H), 3.87-3.91 (m, 1H). |
| Example 2-3 | ASL08 | $NaH_{11}{}^{10}B_{12}S$–chain with $NH_2$, $CO_2H$, $C_8H_{17}$ | $^1$H NMR (D$_2$O): 0.55-1.65 (m, 24H), 2.20-2.50 (m, 2H), 2.85-3.29 (m, 4H), 3.79-3.87 (m, 1H). |
| Example 2-4 | ASL09 | $NaH_{11}{}^{10}B_{12}S$–chain with $NH_2$, $CO_2H$, $C_{10}H_{21}$ | $^1$H NMR (CD$_3$CN): 0.65-1.80 (m, 26H), 2.24-2.48 (m, 2H), 2.82-3.22 (m, 4H), 3.99-4.09 (m, 1H). |
| Example 2-5 | ASL10 | $NaH_{11}{}^{10}B_{12}S$–chain with $NH_2$, $CO_2H$, $C_{12}H_{25}$ | $^1$H NMR (D$_2$O): 0.55-1.65 (m, 28H), 2.20-2.60 (m, 2H), 2.79-3.32 (m, 4H), 4.05-4.20 (m, 1H). |
| Example 2-6 | ASL11 | $NaH_{11}{}^{10}B_{12}S$–chain with $NH_2$, $CO_2H$, $C_{14}H_{29}$ | $^1$H NMR (D$_2$O): 0.55-1.65 (m, 32H), 2.20-2.60 (m, 2H), 2.79-3.32 (m, 4H), 4.05-4.20 (m, 1H). |

TABLE 2-continued

| | Compound name | Structural formula | $^1$H NMR |
|---|---|---|---|
| Example 2-7 | ASL12 | NaH$_{11}$$^{10}$B$_{12}$S(Octyl)-(CH$_2$)$_n$-CH(NH$_2$)CO$_2$H | $^1$H NMR (D$_2$O): 0.55-1.65 (m, 34H), 2.42-2.48 (m, 4H), 2.81-3.06 (m, 4H), 3.69-3.74 (m, 1H). |
| Reference Example | ASL13 | NaH$_{11}$$^{10}$B$_{12}$S$^{\oplus}$(C$_5$H$_{10}$CO$_2$H)-CH(NH$_2$)CO$_2$H | 1H NMR (D$_2$O): 0.80-1.75 (m, 17H), 2.20-2.35 (m, 4H), 2.90-3.20 (m, 2H), 3.65-3.76 (m, 1H), 4.04-410 (m, 2H). |
| Example 2-8 | ASL14 | H$_2$N-CH(COOH)-...-NaH$_{11}$$^{10}$B$_{12}$S-CH$_2$CH$_2$-O-C(=O)-C$_{10}$H$_{21}$ | $^1$H NMR (CD$_3$CN): 0.65-1.80 (m, 30H), 2.24-2.48 (m, 2H), 2.94-3.31 (m, 4H), 3.35-3.81 (m, 5H). |
| Example 2-9 | ASL15 | NaH$_{11}$$^{10}$B$_{12}$S$^{\oplus}$(C$_8$H$_{16}$NH$_2$)-CH(NH$_2$)CO$_2$H | $^1$H NMR (D$_2$O): 0.55-1.65 (m, 23H), 2.27-2.54 (m, 2H), 2.85-3.35 (m, 6H), 4.03-4.16 (m, 1H), 7.59 (br, 2H). |
| Example 2-10 | ASL16 | NaH$_{11}$$^{10}$B$_{12}$S$^{\oplus}$(C$_8$H$_{16}$N$_3$)-CH(NH$_2$)CO$_2$H | $^1$H NMR (CD$_3$CN): 0.77-1.80 (m, 23H), 2.27-2.54 (m, 2H), 2.88-3.29 (m, 4H), 3.49-3.55 (m, 2H), 4.03-4.11 (m, 1H). |
| Example 2-11 | ASL17 | NaH$_{11}$$^{10}$B$_{12}$S$^{\oplus}$(C$_8$H$_{16}$OH)-CH(NH$_2$)CO$_2$H | $^1$H NMR (CD$_3$CN): 0.65-1.80 (m, 23H), 2.24-2.48 (m, 2H), 2.82-3.16 (m, 4H), 3.27 (t, 2H, J = 7.2 Hz Hz), 4.03-4.11 (m, 1H). |
| Example 2-12 | ASL18 | NaH$_{11}$$^{10}$B$_{12}$S$^{\oplus}$(CH$_2$-C$_6$H$_5$)-CH(NH$_2$)CO$_2$H | $^1$H NMR (D$_2$O): 0.85-1.92 (m, 11H), 2.52-2.73 (m, 2H), 3.82-4.46 (m, 3H), 6.98-7.07 (m, 3H), 7.39-7.42 (m, 2H). |

TABLE 3

| | Compound name | Structural formula | $^1$H NMR |
|---|---|---|---|
| Example 2-13 | ASL19 | H$_2$N-CH(COOH)-...-NaH$_{11}$$^{10}$B$_{12}$S$^{\oplus}$-(CH$_2$)$_6$-O-C$_6$H$_4$-NO$_2$ | $^1$H NMR (D$_2$O): 0.55-1.65 (m, 19H), 2.18-2.48 (m, 2H), 2.85-3.35 (m, 6H), 3.68-3.81 (mbr, 2H), 3.82-3.89 (m, 1H), 6.71 (d, 2H, J = 8.0 Hz), 7.87 (d, 2H, J = 8.0 Hz). |

TABLE 3-continued

| Compound name | | Structural formula | $^1$H NMR |
|---|---|---|---|
| Example 2-14 | ASL20 | (structure) | $^1$H NMR (D$_2$O): 0.88-1.78 (m, 19H), 2.14-2.32 (m, 2H), 2.75-3.18 (m, 6H), 3.68-3.74 (mbr, 1H), 3.80 (t, 2H, J = 6.4 Hz), 6.69-6.78 (m, 4H) |
| Example 2-15 | ASL21 | (structure) | $^1$H NMR (D$_2$O): 0.88-1.78 (m, 19H), 2.16-2.36 (m, 2H), 2.75-3.18 (m, 6H), 3.68-3.74 (mbr, 1H), 3.93 (t, 2H, J = 6.4 Hz), 6.88-6.93 (m, 3H), 7.24-7.28 (m, 2H) |
| Example 2-16 | ASL22 | (structure) | $^1$H NMR (D$_2$O): 0.85-1.78 (m, 21H), 2.15-2.26 (m, 2H), 2.81-3.16 (m, 4H), 3.65-3.72 (m, 1H), 3.95 (t, 2H, J = 6.4), 6.90 (d, 2H, J = 8.0 Hz), 7.63 (d, 2H, J = 8.0 Hz). |
| Example 2-17 | ASL23 | (structure) | $^1$H NMR (D$_2$O): 0.55-1.65 (m, 29H), 1.84-2.15 (m, 4H), 2.31-2.55 (m, 8H), 2.65-2.75 (m, 4H), 2.96-3.05 (m, 1H), 3.14-3.21 (m, 1H), 4.09-4.15 (m, 1H). |
| Example 2-18 | ASL24 | (structure) | 1H NMR (DMSO-d6): 0.65-1.55 (brm, 34H), 1.74-1.83 (m, 2H), 1.64-1.72 (m, 4H), 2.78-2.92 (m, 4H), 3.16-3.18 (m, 2H), 4.24-4.33 (m, 3H), 7.94 (s, 1H), 8.24 (br, 2H) |
| Example 2-19 | ASL25 | (structure) | $^1$H NMR (CD$_3$CN): 0.65-1.80 (m, 24H), 2.22-2.44 (mbr, 2H), 3.20-3.53 (m, 3H), 3.66-4.06 (m, 1H), 4.76-4.95 (mbr, 1H). |
| Example 2-20 | ASL26 | (structure) | $^1$H NMR (D$_2$O): 0.55-1.65 (m, 27H), 2.20-2.50 (m, 2H), 2.76-3.19 (m, 4H). |
| Example 2-21 | ASL27 | (structure) | $^1$H NMR (CD$_3$CN): 0.65-1.80 (m, 32H), 2.09-2.38 (m, 4H), 2.75-3.49 (m, 8H), 3.79-4.07 (m, 3H), 6.87-6.91 (m, 2H), 7.15-7.18 (m, 2H). |
| Example 2-22 | ASL28 | (structure) | $^1$H NMR (D$_2$O): 0.55-1.65 (m, 44H), 2.20-2.60 (m, 2H), 2.79-3.32 (m, 4H), 4.05-4.20 (m, 1H). |

TABLE 3-continued

| Compound name | Structural formula | $^1$H NMR |
|---|---|---|
| Example 2-23 ASL29 | NaH$_{11}$$^{10}$B$_{12}$S$^{\oplus}$–C$_8$H$_{17}$ linked to CH$_2$CH$_2$CH(NH$_2$)CO$_2$CH$_3$ | |

TABLE 4

| Compound name | Structural formula | $^1$H NMR |
|---|---|---|
| Example 2-24 AAL01 | H$_2$N–CH(CH$_2$Ph)–C(O)–NH–(CH$_2$)$_3$–S$^{+10}$B$_{12}$H$_{11}$Na / C$_8$H$_{17}$ | $^1$H NMR (DMSO-d6): 0.78-1.58 (mbr, 22H), 1.60-1.84 (m, 4H), 2.68-3.05 (m, 6H), 3.13-3.51 (m, 4H), 3.64-3.82 (m, 1H), 6.90 br, 1H), 7.15-7.37 (m, 5H), 8.33 (t, 1H, J = 5.37 Hz) |
| Example 2-25 AAL02 | H$_2$N–CH(CH$_2$–C$_6$H$_4$–B(OH)$_2$($^{10}$B))–C(O)–NH–(CH$_2$)$_3$–S$^{+10}$B$_{12}$H$_{11}$Na / C$_8$H$_{17}$ | $^1$H NMR (CD$_3$CN): 0.45-1.42 (mbr, 26H), 1.86-1.96 (m, 2H), 2.71-3.07 (m, 6H), 3.16-3.30 (m, 2H), 3.98-4.05 (m, 1H), 6.78-6.96 (m, 1H), 7.22-7.40 (m, 2H), 7.68-7.78 (m, 2H). |
| Example 2-26 AAL03 | H$_2$N–CH(CH$_2$–C$_6$H$_4$–B(OH)$_2$($^{10}$B))–C(O)–NH–CH(COOH)–(CH$_2$)$_2$–S$^{+10}$B$_{12}$H$_{11}$Na / C$_8$H$_{17}$ | $^1$H NMR (DMSO-d6): 0.78-1.75 (mbr, 24H), 1.96-2.22 (m, 2H), 2.68-3.01 (m, 6H), 3.07-3.11 (m, 1H), 3.68-3.76 (m, 1H), 4.09-4.27 (m, 1H), 7.31 (d, 2H, J = 8.0 Hz), 7.71 (d, 2H, J = 8.0 Hz), 8.25-8.46 (brm, 2H). |

Example 3

Production of (S-((5-Hydroxy-4-Oxo-4H-Pyran-2-yl)methyl) octyl)-λ$^3$-Sulfanyl) Undecahydro-Closo-Dodecaborate Sodium Salt S-n-Octyl-thioundecahydro-closo-dodecaborate disodium salt (173 mg, 0.535 mmol) obtained in Example 1 was dissolved in acetonitrile (10 mL), and 2-bromomethyl-5-hydroxy-4H-pyran-on (131 mg, 0.639 mmol) was added thereto, then the mixture was heated under reflux for 24 hours. After concentrating the reaction mixture to dryness, acetone (100 mL) was added thereto and the insoluble materials were removed by filtration. After concentrating the filtrate, the resulting mixture was purified by ODS column chromatography (H$_2$O-70% H$_2$O/MeCN) and freeze-dried to obtain the objective compound (184 mg, 80.8%) as a colorless powder. $^1$H NMR (DMSO-d$_6$): 0.60-1.85 (m, 26H), 3.05-3.09 (m, 2H), 4.12-4.31 (m, 2H), 6.61 (s, 1H), 7.09 (s, 1H).

In the same manner, the compounds shown in the following Table 5 were synthesized.

TABLE 5

| | Compound name | Structural formula | ¹H NMR |
|---|---|---|---|
| Reference Example | KA01 | 5-hydroxy-2-(($^{10}B_{12}H_{11}Na_2$)-S-methyl)-4H-pyran-4-one | |
| Reference Example | KA02 | 5-hydroxy-2-((2-cyanoethyl)($^{10}B_{12}H_{11}Na_2$)-S-methyl)-4H-pyran-4-one | |
| Reference Example | KA03 | 5-hydroxy-2-((methyl)($^{10}B_{12}H_{11}Na$)-S-methyl)-4H-pyran-4-one, with CH₃ on S | 1H NMR (CD₃CN): 0.74-1.78 (m, 11H), 2.52 (s, 3H), 3.89 (d, 1H, J = 14.4 Hz), 4.12 (d, 1H, J = 14.4 Hz), 6.49-6.51 (brm, 1H), 7.93 (s, 1H). |
| Reference Example | KA04 | 5-hydroxy-2-(($C_4H_9$)($^{10}B_{12}H_{11}Na$)-S-methyl)-4H-pyran-4-one | 1H NMR (CD₃CN): 0.64-1.78 (m, 18H), 2.89-3.16 (m, 2H), 3.97 (d, 1H, J = 14.8 Hz), 4.19 (d, 1H, J = 14.8 Hz), 6.49-6.52 (brm, 1H), 7.94 (s, 1H). |
| Example 3-2 | KA05 | 5-hydroxy-2-(($C_6H_{13}$)($^{10}B_{12}H_{11}Na$)-S-methyl)-4H-pyran-4-one | 1H NMR (D₂O): 0.55-1.85 (m, 20H), 3.04-3.14 (m, 2H), 4.12-4.22 (m, 2H), 6.58-6.62 (brm, 1H), 8.01 (s, 1H). |
| Example 3-3 | KA06 | 5-hydroxy-2-(($C_8H_{17}$)($^{10}B_{12}H_{11}Na$)-S-methyl)-4H-pyran-4-one | 1H NMR (D₂O): 0.55-1.85 (m, 24H), 3.04-3.14 (m, 2H), 4.12-4.22 (m, 2H), 6.58-6.62 (brm, 1H), 7.99 (s, 1H). |
| Example 3-4 | KA07 | 5-hydroxy-2-(($C_{10}H_{21}$)($^{10}B_{12}H_{11}Na$)-S-methyl)-4H-pyran-4-one | 1H NMR (D₂O): 0.55-1.85 (m, 28H), 3.04-3.14 (m, 2H), 4.12-4.22 (mbr, 2H), 6.58-6.62 (brm, 1H), 7.97 (s, 1H). |
| Example 3-5 | KA08 | 5-hydroxy-2-(($C_{12}H_{25}$)($^{10}B_{12}H_{11}Na$)-S-methyl)-4H-pyran-4-one | 1H NMR (D₂O): 0.55-1.85 (m, 32H), 3.04-3.14 (m, 2H), 4.12-4.22 (mbr, 2H), 6.60 (br, 1H), 7.96 (s, 1H). |
| Example 3-6 | KA09 | 5-hydroxy-2-(($C_{14}H_{29}$)($^{10}B_{12}H_{11}Na$)-S-methyl)-4H-pyran-4-one | 1H NMR (D₂O): 0.55-1.85 (m, 36H), 3.04-3.14 (m, 2H), 4.12-4.22 (mbr, 2H), 6.60 (br, 1H), 7.96 (s, 1H). |

TABLE 5-continued

| | Compound name | Structural formula | $^1$H NMR |
|---|---|---|---|
| Example 3-7 | KA10 | (5-hydroxy-4-oxo-4H-pyran-2-yl)methyl-S(C$_{16}$H$_{33}$)-$^{10}$B$_{12}$H$_{11}$Na | 1H NMR (D$_2$O): 0.55-1.85 (m, 40H), 3.04-3.14 (m, 2H), 4.12-4.22 (mbr, 2H), 6.60 (br, 1H), 7.96 (s, 1H). |
| Example 3-8 | KA11 | (5-hydroxy-4-oxo-4H-pyran-2-yl)methyl-S(C$_6$H$_{16}$OH)-$^{10}$B$_{12}$H$_{11}$Na | 1H NMR (D$_2$O): 0.65-1.85 (m, 23H), 2.96-3.17 (m, 2H), 3.44-3.55 (m, 2H), 4.10-4.25 (m, 2H), 6.52-6.65 (brm, 1H), 8.05 (s, 1H). |
| Example 3-9 | KA12 | (5-hydroxy-4-oxo-4H-pyran-2-yl)methyl-S(C$_5$H$_{10}$COOH)-$^{10}$B$_{12}$H$_{11}$Na | 1H NMR (D$_2$O): 0.65-1.85 (m, 15H), 2.24-2.31 (m, 2H), 2.97-3.18 (m, 2H), 4.04-4.26 (m, 4H), 6.59 (s, 1H), 7.96 (s, 1H). |
| Example 3-10 | KA13 | (5-hydroxy-4-oxo-4H-pyran-2-yl)methyl-S(CH$_2$CH$_2$OCH$_2$CH$_2$OCH$_2$CH$_2$OCH$_2$CH$_2$OCH$_3$)-$^{10}$B$_{12}$H$_{11}$Na | 1H NMR (D$_2$O): 0.55-1.85 (mbr, 11H), 3.29 (s, 3H), 3.55-3.64 (m, 14H), 3.75-3.88 (m, 2H), 4.16-4.44 (m, 2H), 6.63-6.66 (brm, 1H), 8.04 (s, 1H). |

The compounds shown in Table 6 were synthesized in the same manner as in Examples 1 to 3.

TABLE 6

| | Compound name | Structural formula | $^1$H NMR |
|---|---|---|---|
| Example 4-1 | GLC01 | Tetra-O-acetyl-glucopyranosyl-S(C$_8$H$_{17}$)-$^{10}$B$_{12}$H$_{11}$Na | $^1$H NMR (D$_2$O): 0.55-1.90 (m, 26H), 2.03 (s, 3H), 2.10 (s, 6H), 2.20 (s, 3H), 3.19-3.37 (brm, 2H), 3.71-3.80 (mbr, 1H), 4.08-4.15 (m, 2H), 4.32-4.36 (m, 1H), 5.07 (t, J = 4.8 Hz, 1H), 6.48 (br, 1H). |
| Example 4-2 | GLC02 | Glucopyranosyl-S(C$_8$H$_{17}$)-$^{10}$B$_{12}$H$_{11}$Na | $^1$H NMR (D$_2$O): 0.55-1.90 (m, 26H), 2.60-3.48 (brm, 2H), 3.58-4.05 (m, 2H), 4.82-4.90 (m, 1H), 5.89-5.92 (m, 1H). |
| Example 4-3 | HQ01 | HO-C$_6$H$_4$-O-(CH$_2$)$_n$-S$^{\oplus}$(CH$_3$)-$^{10}$B$_{12}$H$_{11}$Na | 1H NMR (DMSO-d6): 0.45-1.42 (mbr, 25H), 2.21 (s, 3H), 3.89 (d, 2H, J = 14.4 Hz), 3.53 (t, 2H, J = 6.4 Hz), 6.35 (d, 2H, J = 8.8 Hz), 6.42 (d, 2H, J = 8.8 Hz). |
| Example 4-4 | HQ02 | HO-C$_6$H$_4$-O-(CH$_2$)$_n$-S$^{\oplus}$(C$_8$H$_{17}$)-$^{10}$B$_{12}$H$_{11}$Na | 1H NMR (CD$_3$CN): 0.55-1.78 (mbr, 38H), 2.75-2.82 (m, 2H), 2.96-3.03 (m, 2H), 3.53 (t, 2H, J = 6.4 Hz), 6.69-6.76 (m, 4H). |

TABLE 6-continued

| Compound name | | Structural formula | $^1$H NMR |
|---|---|---|---|
| Example 4-5 | REB01 | [structure: resveratrol derivative with O-C6H12-S⊕($^{10}$B$_{12}$H$_{11}$)Na, C8H17] | 1H NMR (DMSO-d6): 0.45-1.78 (mbr, 34H), 2.80-2.95 (m, 4H), 3.91-3.98 (m, 2H), 6.20 (s, 1H), 6.51 (d, 1H, J = 9.6 Hz), 6.57 (d, 1H, J = 9.6 Hz), 6.75 (d, 2H, J = 8.0 Hz), 6.84-7.05 (m, 2H), 7.40 (d, 2H, J = 8.0 Hz), 9.37 (s, 1H), 9.57 (s, 1H). . |
| Example 4-6 | DBP01 | [structure: pyrazolopyrimidine derivative with C8H17-S⊕($^{10}$B$_{12}$H$_{11}$)Na$_2$, C8H16, NEt2] | $^1$H NMR (D$_2$O): 0.65-1.65 (m, 42H), 1.63-1.77 (m, 4H), 2.26 (s, 2H), 2.49 (s, 3H), 2.70 (s, 3H), 2.81-2.88 (m, 2H), 3.28 (q, 2H, J = 7.2 Hz), 3.51 (q, 2H, J = 7.2 Hz), 3.84 (s, 1H), 4.00 (t, 2H, J = 6.0 Hz), 6.84 (s, 1H), 7.01 (d, 2H, J = 8.8 Hz), 7.66 (d, 2H, J = 8.8 Hz). |
| Example 4-7 | DBP02 | [structure: pyrazolopyrimidine derivative with C8H17-S⊕($^{10}$B$_{12}$H$_{11}$)Na$_2$, C3H6, NEt2] | $^1$H NMR (D$_2$O): 0.65-1.65 (m, 32H), 1.70-1.77 (m, 2H), 2.09 (s, 2H), 2.49 (s, 3H), 2.69 (s, 3H), 2.81-2.88 (m, 1H), 2.99-3.07 (m, 2H), 3.18-3.24 (m, 1H), 3.34 (q, 2H, J = 7.2 Hz), 3.50 (q, 2H, J = 7.2 Hz), 3.86 (s, 1H), 4.13 (t, 2H, J = 6.0 Hz), 6.67 (s, 1H), 7.01 (d, 2H, J = 8.8 Hz), 7.70 (d, 2H, J = 8.8 Hz). |
| Example 4-8 | CFA01 | [structure: diacetoxy cinnamamide with S$^{+10}$B$_{12}$H$_{11}$Na, C8H17] | 1H NMR (CD$_3$CN): 0.78-1.78 (mbr, 26H), 1.95-2.02 (m, 2H), 2.26 (s, 3H), 2.27 (s, 3H), 2.76-2.88 (m, 2H), 2.99-3.08 (m, 2H), 3.53 (m, 2H), 3.23-3.42 (m, 2H), 7.23 (d, 1H, J = 8.4 Hz), 7.41-7.48 (m, 3H). |
| Example 4-9 | 5ALA01 | [structure: 5-aminolevulinic acid derivative with C8H17-S$^{+10}$B$_{12}$H$_{11}$Na] | 1H NMR (DMSO-d6): 0.78-1.54 (mbr, 25H), 1.59-1.98 (m, 4H), 2.07-2.27 (m, 2H), 2.32-2.45 (m, 1H), 2.53-2.62 (m, 1H), 2.78-3.16 (m, 6H), 4.02-4.13 (m, 1H). |

(Biological Evaluation 1)

Cytotoxicity, uptake into cancer cells, and cell killing effect by neutron irradiation are evaluated by performing the following biological assays on the boron-containing compounds (boron agents) obtained in the examples.

Cytotoxicity Test (WST-8)

Using a 96-well microplate, rat glioma cells (C6) or melanoma cells (B16) were seeded at a density of 1.5×10$^4$ cells/ml per well and cultured at room temperature (37° C., 5% CO$_2$) for 24 hours. The culture fluid was taken out by suction, and culture fluids containing the boron-containing compound obtained in the example at various concentrations were added to each well in an amount of 100 μL each. After culturing at room temperature (37° C., 5% CO$_2$) for 24 hours, the culture fluid was taken out by suction, 100 μL of WST-8 solution was added respectively, and the resulting mixture was further cultured at room temperature (37° C., 5% CO$_2$) for 4 hours. Using a microplate reader, the absorbance at a wavelength of 450 nm (reference wavelength: 655 nm) was measured, and the absorbance of wells not containing cells was employed as background control. Each IC$_{50}$ value was determined thereby.

Among the boron-containing compounds obtained in the examples, the compounds having R4 as kojic acid or amino acid showed at least about the same degree of cytotoxicity as 4-borono-L-phenylalanine (L-BPA).

(Biological Evaluation 2)

Uptake Test of Boron-Containing Compound into Tumor Cells

Rat glioma cells (C6) or melanoma cells (B16) of $1.5 \times 10^7$ cells were seeded and cultured at room temperature (37° C., 5%. $CO_2$) for 24 hours. The culture fluid was taken out by suction, a culture fluid containing 0.2 mM of each boron agent was added thereto, and the mixture was further cultured at room temperature (37° C., 5% $CO_2$) for 24 hours. After taking out the culture fluid by suction, the cells were washed three times with PBS and then treated with trypsin to recover the cells. The number of the cells recovered was counted, and $HClO_4$ (60%, 0.3 ml) and $H_2O_2$ (31%, 0.6 ml) were heated at 75° C. for one hour to prepare an ashing solution. The ashing solution was filtered by using a membrane filter, and the intracellular boron concentration was determined by measuring the boron concentration in the solution using ICP-AES.

Figure 3:
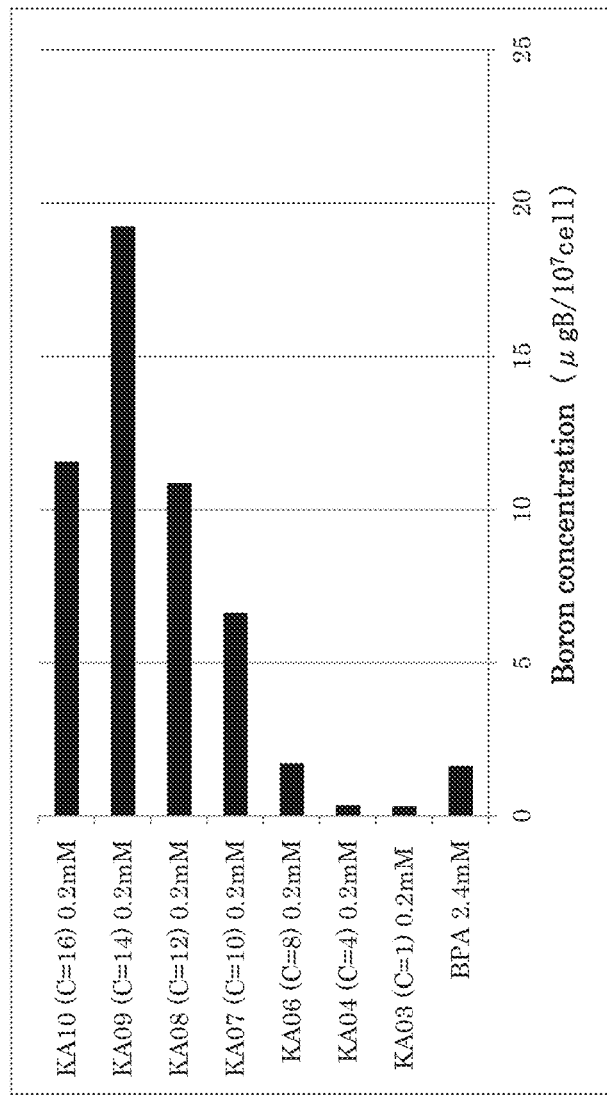
FIG. 3 is a graph showing the results of an uptake test on the boron-containing compound of the present invention and other compounds into tumor cells.

The results of the uptake test of the boron-containing compounds of the examples are shown in FIGS. 1 and 3. Here, 4-borono-L-phenylalanine (L-BPA) used for clinical studies of BNCT was set as a comparative control.

As a result, it was found that, when the alkyl chain has a certain length or longer, the compound of the present invention is taken into cells more than the same level by treatment at a lower concentration, as compared with BPA. Also, when C14 or higher, agent uptake tended to decrease. Since the toxicity of the agent tends to increase in proportion to the length of the alkyl chain, it is considered that, among the compounds experimented, the length of the alkyl chain is particularly preferably about $C_6$ to $C_{14}$.

A similar experiment was performed using rat glioma (F98).

Figure 2:
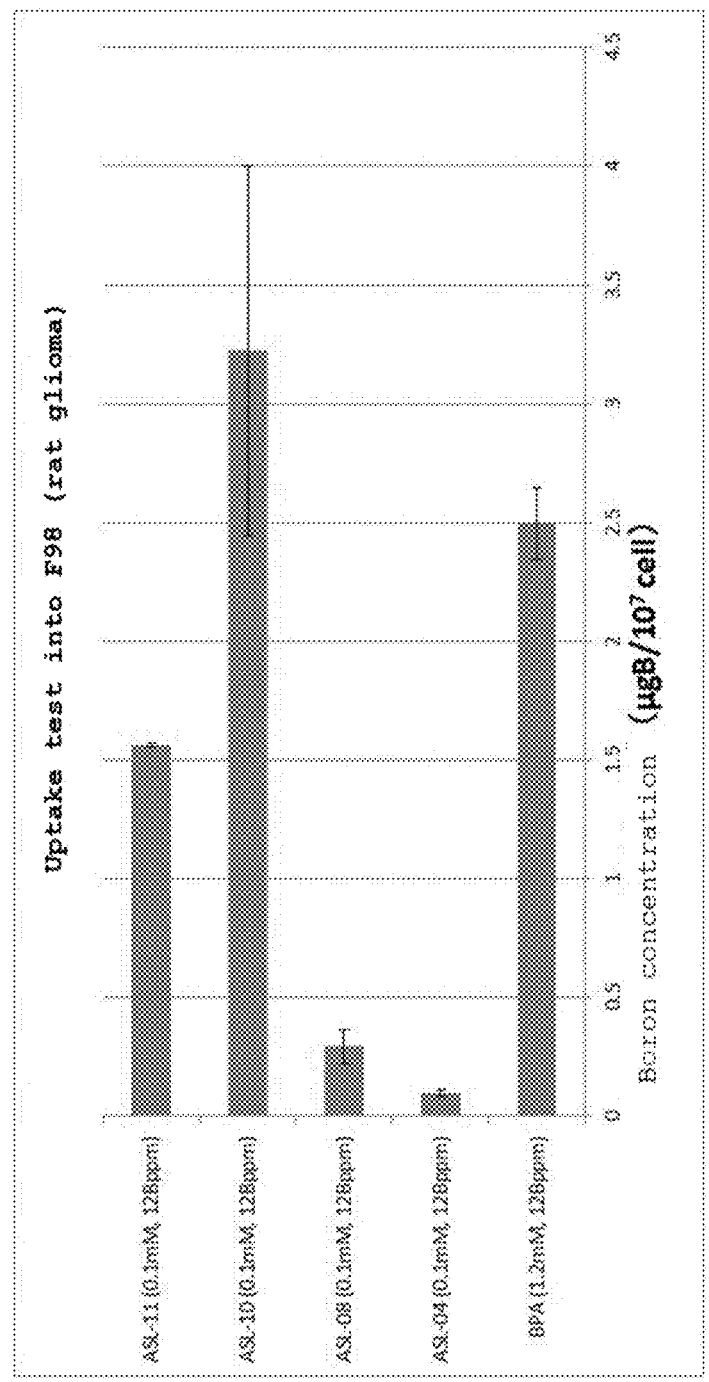
FIG. 2 is a graph showing the results of an uptake test on the boron-containing compound of the present invention and other compounds into rat glioma cells.

As a result, the boron-containing compound of the present invention was efficiently taken into the cells (FIG. 2)

The results on other uptake of the main compounds are shown in Table 7 below. In the table, it means that ○: uptake is higher than BPA, Δ: uptake is about the same as BPA, and x: uptake is lower than BPA.

TABLE 7

| Compound name | Structural formula | Comparison of uptake amount into B16 mouse melanoma cells versus same dose of BPA |
|---|---|---|
| ABS01 | $CH_3$—$S^{10}B_{12}H_{11}Na_2$ | x |
| ABS02 | $C_4H_9$—$S^{10}B_{12}H_{11}Na_2$ | x |
| ABS03 | $C_6H_{13}$—$S^{10}B_{12}H_{11}Na_2$ | Δ |
| ABS04 | $C_8H_{17}$—$S^{10}B_{12}H_{11}Na_2$ | ○ |
| ABS05 | $C_{10}H_{21}$—$S^{10}B_{12}H_{11}Na_2$ | ○ |
| ABS06 | $C_{12}H_{25}$—$S^{10}B_{12}H_{11}Na_2$ | ○ |
| ASL01 | $Na_2H_{11}{}^{10}B_{12}S$—(CH$_2$)$_2$—CH(NH$_2$)—CO$_2$H | x |
| ASL04 | $NaH_{11}{}^{10}B_{12}S^{\oplus}$(with alkyl branch)—CH(NH$_2$)—CO$_2$H | x |
| ASL05 | $NaH_{11}{}^{10}B_{12}S^{\oplus}$(with longer alkyl branch)—CH(NH$_2$)—CO$_2$H | x |

TABLE 7-continued

| Compound name | Structural formula | Comparison of uptake amount into B16 mouse melanoma cells versus same dose of BPA |
|---|---|---|
| ASL06 | NaH$_{11}$$^{10}$B$_{12}$S$^{\oplus}$—(CH$_2$CH$_2$)—CH(NH$_2$)—CO$_2$Et, with isobutyl on S | x |
| ASL07 | NaH$_{11}$$^{10}$B$_{12}$S$^{\oplus}$ with C$_6$H$_{13}$, CH(NH$_2$)CO$_2$H | Δ |
| ASL08 | NaH$_{11}$$^{10}$B$_{12}$S$^{\oplus}$ with C$_8$H$_{17}$, CH(NH$_2$)CO$_2$H | Δ |
| ASL09 | NaH$_{11}$$^{10}$B$_{12}$S$^{\oplus}$ with C$_{10}$H$_{21}$, CH(NH$_2$)CO$_2$H | ○ |
| ASL10 | NaH$_{11}$$^{10}$B$_{12}$S$^{\oplus}$ with C$_{12}$H$_{25}$, CH(NH$_2$)CO$_2$H | ○ |
| ASL11 | NaH$_{11}$$^{10}$B$_{12}$S$^{\oplus}$ with C$_{14}$H$_{29}$, CH(NH$_2$)CO$_2$H | ○ |
| KA01 | 5-hydroxy-4H-pyran-4-one with CH$_2$—S$^{10}$B$_{12}$H$_{11}$Na$_2$ | x |
| KA03 | 5-hydroxy-4H-pyran-4-one with CH$_2$—S$^{+}$(CH$_3$)$^{10}$B$_{12}$H$_{11}$Na | x |
| KA04 | 5-hydroxy-4H-pyran-4-one with CH$_2$—S$^{+}$(C$_4$H$_9$)$^{10}$B$_{12}$H$_{11}$Na | x |
| KA05 | 5-hydroxy-4H-pyran-4-one with CH$_2$—S$^{+}$(C$_6$H$_{13}$)$^{10}$B$_{12}$H$_{11}$Na | Δ |

TABLE 7-continued
| Compound name | Structural formula | Comparison of uptake amount into B16 mouse melanoma cells versus same dose of BPA |
|---|---|---|
| KA06 | 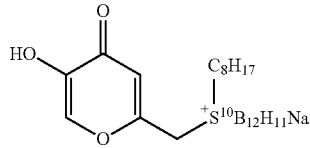 | Δ |
| KA07 | 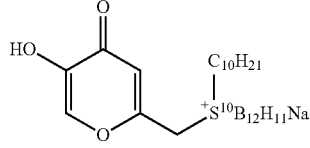 | ○ |
| KA08 | 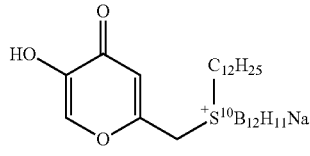 | ○ |
| KA09 | 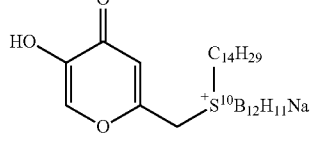 | ○ |
| KA10 | 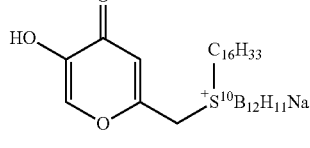 | ○ |
| AAL01 | 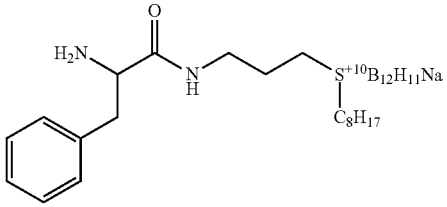 | ○ |
| AAL02 | 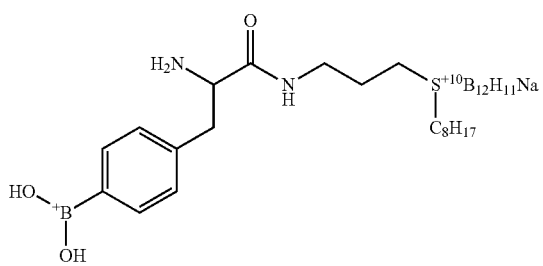 | ○ |
| GLC01 | 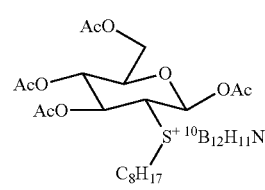 | Δ |

TABLE 7-continued

| Compound name | Structural formula | Comparison of uptake amount into B16 mouse melanoma cells versus same dose of BPA |
|---|---|---|
| GLC02 | (β-D-glucopyranose with S$^+$ $^{10}$B$_{12}$H$_{11}$Na and C$_8$H$_{17}$ substituent at C2) | ○ |
| HQ01 | HO-C$_6$H$_4$-O-(CH$_2$)$_n$-S($^{10}$B$_{12}$H$_{11}$Na)(CH$_3$) | x |
| HQ02 | HO-C$_6$H$_4$-O-(CH$_2$)$_n$-S($^{10}$B$_{12}$H$_{11}$Na)(C$_8$H$_{17}$) | Δ |
| REB01 | Resveratrol-O-(CH$_2$)$_n$-S($^{10}$B$_{12}$H$_{11}$Na)(C$_8$H$_{17}$) | ○ |
| DBP01 | 5,7-dimethyl-pyrazolo[1,5-a]pyrimidine with 2-(4-(OC$_8$H$_{16}$-S($^{10}$B$_{12}$H$_{11}$Na$_2$)(C$_8$H$_{17}$))phenyl) and 3-CH$_2$C(O)NEt$_2$ | ○ |
| DBP02 | 5,7-dimethyl-pyrazolo[1,5-a]pyrimidine with 2-(4-(OC$_3$H$_6$-S($^{10}$B$_{12}$H$_{11}$Na$_2$)(C$_8$H$_{17}$))phenyl) and 3-CH$_2$C(O)NEt$_2$ | ○ |
| CFA01 | AcO-C$_6$H$_3$(OAc)-CH=CH-C(O)NH-(CH$_2$)$_3$-S$^+$($^{10}$B$_{12}$H$_{11}$Na)(C$_8$H$_{17}$) | Δ |

TABLE 7-continued

| Compound name | Structural formula | Comparison of uptake amount into B16 mouse melanoma cells versus same dose of BPA |
|---|---|---|
| 5ALA01 | 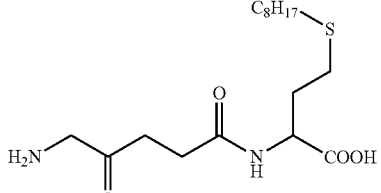 | ○ |

(Biological Evaluation 3) Cell Killing Effect for Tumor Cells Subjected By Neutron Irradiation $5.0 \times 10^6$ cells are seeded and cultured at room temperature (37° C., 5% $CO_2$) for 24 hours. This culture fluid was taken out by suction, a culture fluid containing 2.0 mM of each boron agent is added thereto, and the mixture is further cultured at room temperature (37° C., 5% $CO_2$) for 6 hours. After taking out the culture fluid by suction, the cells were washed three times with PBS and then treated with trypsin to recover the cells. The recovered cells are suspended in the culture fluid, adjusted to a density of $5.0 \times 10^3$ cells/ml, and 1 ml of this suspension is transferred to a Teflon (registered trademark) tube. The Teflon (registered trademark) tube containing the cell solution is irradiated with thermal neutrons at 0 to $4.3 \times 10^{12}$ $cm^{-2}$, and the cells are seeded in 6 ml of the culture fluid at 300 cells each. After culturing at room temperature (37° C., 5% $CO_2$) for 9 days, the colony was immobilized with ethanol and stained with 0.1% crystal violet, and the number of colonies was counted for comparison of cell killing effect.

The invention claimed is:

1. A boron-containing compound represented by the following formula I or a pharmaceutically acceptable salt thereof:

[Formula 1]

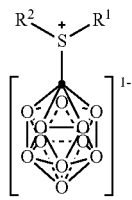

(I)

wherein a black circle represents B atom, white circles represent B—H;

—$R^1$ represents —$(CH_2)n$-$X^1$—$R^3$ (n represents an integer of 0 to 6; $X^1$ represents O, S, NH, S—S, O—CO, NHCO or SCO, or does not exist; $R^3$ represents $C_6$-$C_{20}$ alkyl, hydroxy $C_6$-$C_{20}$ alkyl, amino $C_6$-$C_{20}$ alkyl, azido $C_6$-$C_{20}$ alkyl, hydroxycarbonyl $C_6$-$C_{20}$ alkyl, substituted or unsubstituted phenoxy $C_6$-$C_{20}$ alkyl, substituted or unsubstituted phenylthiourea $C_6$-$C_{20}$ alkyl, or a substituted or unsubstituted benzyl group), or a group having a repeating sequence of —$(CH_2)_2$—O— 3 times or more and 10 times or less and having a methyl group or an ethyl group at the end on the oxygen atom side; and —$R^2$ represents —$(CH_2)m$-$X^2$—$R^4$ (m represents an integer from 0 to 8; $X^2$ represents O, S, NH, S—S, O—CO, NHCO or SCO, or does not exist; $R^4$ represents a tumor recognition moiety selected from the group consisting of amino acid amide, 5-aminolevulinic acid, kojic acid or salts thereof, hydroquinone or salts thereof, resveratrol or salts thereof, DPA (dimethylpyrazolopyrimidine acetamide) type TSPO (translocator protein) ligand, caffeic acid or salts thereof, monosaccharides or salts thereof, and nucleic acids or constituents thereof or salts thereof).

2. A pharmaceutically acceptable salt of a boron-containing compound, represented by the following formula II

[Formula 2]

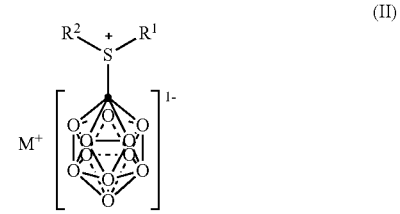

(II)

wherein —$R^1$ represents —$(CH_2)n$-$X^1$—$R^3$ (n represents an integer of 1 to 4; $X^1$ represents O, S, NH, S—S, O—CO, NHCO or SCO; and $R^3$ represents $C_6$-$C_{20}$ alkyl); and $M^+$ represents an alkali metal ion, an ammonium ion or a tetraalkylammonium ion ($NR^{4+}$), or a tetraphenylphosphonium ion —$R^2$ represents —$(CH_2)m$-$X^2$—$R^4$ (m represents an integer from 0 to 8; $X^2$ represents O, S, NH, S—S, O—CO, NHCO or SCO, or does not exist; $R^4$ represents a tumor recognition moiety selected from the group consisting of amino acids, amino acid amide, 5-aminolevulinic acid, kojic acid or salts thereof, hydroquinone or salts thereof, resveratrol or salts thereof, DPA (dimethylpyrazolopyrimidine acetamide) type TSPO (translocator protein) ligand, caffeic acid or salts thereof, monosaccharides or salts thereof, and nucleic acids or constituents thereof or salts thereof).

3. The boron-containing compound or a pharmaceutically acceptable salt thereof according to claim 1, wherein —$R^2$ represents —$(CH_2)m$-$X^2$—$R^4$ (m represents an integer from 0 to 8; $X^2$ represents O, S, NH, S—S, O—CO, NHCO or SCO, or does not exist; and —$R^4$ represents a kojic acid represented by

[Formula 3]

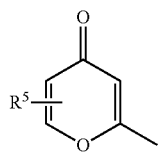

wherein $R^5$ is a hydroxyl group or a salt thereof).

4. The boron-containing compound or a pharmaceutically acceptable salt thereof according to claim 1, wherein
—$R^2$ represents —$(CH_2)m$-$X^2$—$R^4$ (m represents an integer from 0 to 8; $X^2$ represents O, S, NH, S—S, O—CO, NHCO or SCO, or does not exist; and —$R^4$ represents

[Formula 4]

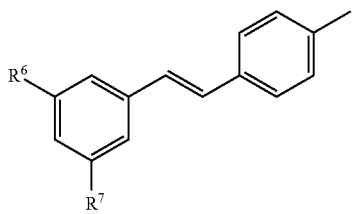

wherein $R^6$ and $R^7$ may be the same or different, and represent a group selected from a hydroxyl group and salts thereof).

5. The pharmaceutically acceptable salt of a boron-containing compound according to claim 2, wherein
—$R^2$ represents —$(CH_2)m$-$X^2$—$R^4$ (m represents an integer from 0 to 8; $X^2$ represents O, S, NH, S—S, O—CO, NHCO or SCO, or does not exist; and —$R^4$ represents a compound represented by either

[Formula 5]

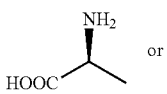

[Formula 6]

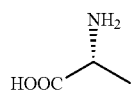

or a salt thereof).

6. The boron-containing compound or a pharmaceutically acceptable salt thereof according to claim 1, wherein
—$R^2$ represents —$(CH_2)m$-$X^2$—$R^4$ (m represents an integer from 0 to 8; $X^2$ represents O, S, NH, S—S, O—CO, NHCO or SCO, or does not exist; and —$R^4$ is any one group selected from groups represented by

[Formula 7]

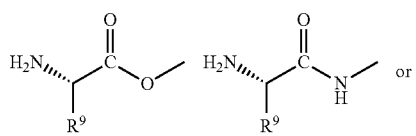

[Formula 8]

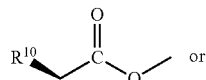

wherein $R^9$ is hydrogen, methyl, isobutyl, 1-propyl, isopropyl, tert-butyl, ethyl, carbonylmethyl, 2-carbonylethyl, hydroxymethyl, hydroxy, mercaptomethyl, methylthioethyl, 2-amino-2-oxoethyl, 3-amino-3-oxopropyl, substituted or unsubstituted benzyl, 4-hydroxybenzyl, 3-aminopropyl, 4-aminobutyl, 3-guanidinopropyl, indolylmethyl, imidazolemethyl, substituted or unsubstituted phenyl, 1-hydroxyethyl or para-boronophenyl, and salts thereof).

7. The boron-containing compound or a pharmaceutically acceptable salt thereof according to claim 1, wherein
—$R^2$ represents —$(CH_2)m$-$X^2$—$R^4$ (m represents an integer from 0 to 8; $X^2$ represents O, S, NH, S—S, O—CO, NHCO or SCO, or does not exist; and —$R^4$ is any one group selected from groups represented by

[Formula 9]

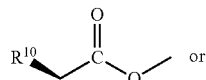

or

[Formula 10]

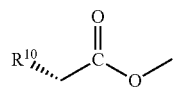

wherein —$R^{10}$ represents

[Formula 11]

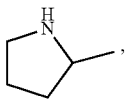

and salts thereof).

8. The boron-containing compound or a pharmaceutically acceptable salt thereof according to claim 1, wherein
—$R^2$ represents —$(CH_2)m$-$X^2$—$R^4$ (m represents an integer from 0 to 8; $X^2$ represents O, S, NH, S—S, O—CO, NHCO or SCO, or does not exist; and —$R^4$ is any one group selected from groups represented by

[Formula 12]

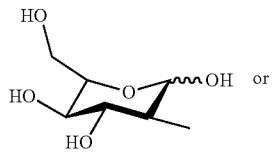 or

-continued

[Formula 13]

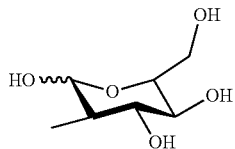

and salts thereof).

9. The boron-containing compound or a pharmaceutically acceptable salt thereof according to claim 1, wherein
—$R^2$ represents —$(CH_2)$m-$X^2$—$R^4$ (m represents an integer from 0 to 8; $X^2$ represents O, S, NH, S—S, O—CO, NHCO or SCO, or does not exist; and —$R^4$ is any one group selected from groups represented by

[Formula 14]

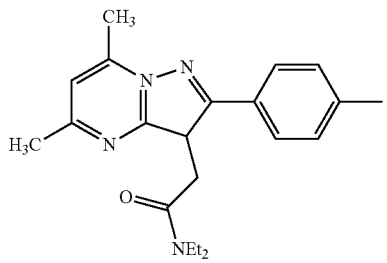

and salts thereof).

10. A boron-containing compound represented by the following formula I or a pharmaceutically acceptable salt thereof:

[Formula 15]

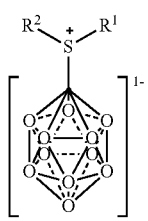 (I)

wherein a black circle represents B atom, white circles represent B—H;
$R^2$ does not exist, and
—$R^1$ is —$(CH_2)$n-$X^1$—$R^3$ (n represents 0 integer; $X^1$ does not exist; and $R^3$ represents $C_6$ to $C_{20}$ alkyl).

11. A method for producing the boron-containing compound of the following formula,

[Formula 17]

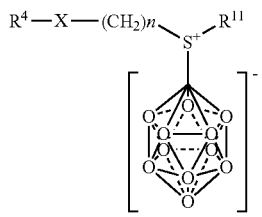

or a pharmaceutically acceptable salt thereof, comprising the step of reacting a compound represented by

[Formula 16]

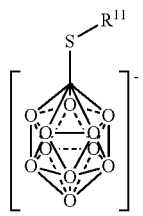

black circle: B, white circle: B—H,
(—$R^{11}$ represents —$(CH_2)$n-$X^1$—$R^3$ (n represents an integer of 0 to 6; $X^1$ represents O, S, NH, S—S, O—CO, NHCO or SCO, or does not exist; $R^3$ represents $C_6$-$C_{20}$ alkyl, hydroxy $C_6$-$C_{20}$ alkyl, amino $C_6$-$C_{20}$ alkyl, azido $C_6$-$C_{20}$ alkyl, hydroxycarbonyl $C_6$-$C_{20}$ alkyl, substituted or unsubstituted phenoxy C6-C20 alkyl, substituted or unsubstituted phenylthiourea C6-C20 alkyl, or a substituted or unsubstituted benzyl group), or a group having a repeating sequence of —$(CH_2)_2$—O— 3 times or more and 10 times or less and having a methyl group or an ethyl group at the end on the oxygen atom side); with $R^{12}$—$(CH_2)$m-$X^2$—$R^4$ (m represents an integer from 0 to 8; $X^2$ represents O, S, NH, S—S, O—CO, NHCO or SCO, or does not exist; $R^4$ represents a tumor recognition moiety selected from the group consisting of amino acid amide, 5-aminolevulinic acid, kojic acid or salts thereof, hydroquinone or salts thereof, resveratrol or salts thereof, DPA (dimethylpyrazolopyrimidine acetamide) type TSPO (translocator protein) ligand, caffeic acid or salts thereof, monosaccharides or salts thereof, and nucleic acids or constituents thereof or salts thereof, and $R^{12}$ represents a halogen).

12. A pharmaceutical composition comprising one or more compounds according to claim 1.

13. The pharmaceutical composition according to claim 12, which is used for treating cancer with BNCT.

* * * * *